United States Patent
Haralambidis

(10) Patent No.: US 11,969,590 B2
(45) Date of Patent: *Apr. 30, 2024

(54) DEVICE FOR ELECTRICAL STIMULATION OF PERIDONTAL COMPLEX AND SURROUNDING TISSUE

(71) Applicant: Cosmo Haralambidis, Cranston, RI (US)

(72) Inventor: Cosmo Haralambidis, Cranston, RI (US)

( * ) Notice: Subject to any disclaimer, the term of this patent is extended or adjusted under 35 U.S.C. 154(b) by 11 days.

This patent is subject to a terminal disclaimer.

(21) Appl. No.: 17/353,887

(22) Filed: Jun. 22, 2021

(65) Prior Publication Data

US 2022/0001171 A1    Jan. 6, 2022

Related U.S. Application Data

(63) Continuation of application No. 16/220,519, filed on Dec. 14, 2018, now Pat. No. 11,103,696, which is a
(Continued)

(51) Int. Cl.
*A61N 1/05* (2006.01)
*A61C 7/00* (2006.01)
(Continued)

(52) U.S. Cl.
CPC ............ *A61N 1/0548* (2013.01); *A61C 7/008* (2013.01); *A61C 19/06* (2013.01); *A61N 1/0472* (2013.01);
(Continued)

(58) Field of Classification Search
CPC ................ A61N 1/0548; A61N 1/0472; A61N 1/36021; A61C 19/06
(Continued)

(56) References Cited

U.S. PATENT DOCUMENTS

| 1,525,857 A | 2/1925 | Eidmann |
| 2,151,738 A | 3/1939 | Buhse |

(Continued)

FOREIGN PATENT DOCUMENTS

| CA | 2999710 A1 | 11/2016 |
| CN | 1972729 A | 5/2007 |

(Continued)

OTHER PUBLICATIONS

International Preliminary Report on Patentability for International Application PCT/US2019/065839, Report dated Jun. 8, 2021, dated Jun. 24, 2021, 8 Pgs.

(Continued)

*Primary Examiner* — Alyssa M Alter
(74) *Attorney, Agent, or Firm* — Patent GC LLC

(57) ABSTRACT

A device for electrical stimulation of one or more components of the periodontal complex and surrounding tissue of a tooth, for uses such as reducing orthodontic pain and encouraging tooth movement, has electrodes of a rigid, electrically conductive material in a fixed spatial relationship configured for application to oral mucosa and attached gingiva adjacent to, and along a periodontal ligament of, a root structure of a single tooth. An electrical circuit is configured for electrical connection to the at least two electrodes. The electrical circuit has an output providing a subsensory electrical stimulus comprising a waveform in accordance with predetermined stimulation parameters. After the electrodes are applied to the oral mucosa and attached gingiva adjacent to, and along the periodontal ligament of, a root structure of the tooth, a switch, when activated, activates the electrical circuit to output the electrical stimulus through the at least two electrodes.

19 Claims, 13 Drawing Sheets

Related U.S. Application Data continuation-in-part of application No. 15/791,462, filed on Oct. 24, 2017, now Pat. No. 10,391,302, which is a continuation of application No. 15/147,234, filed on May 5, 2016, now Pat. No. 9,855,418.

(60) Provisional application No. 62/157,053, filed on May 5, 2015.

(51) Int. Cl.
*A61C 19/06* (2006.01)
*A61N 1/04* (2006.01)
*A61N 1/36* (2006.01)

(52) U.S. Cl.
CPC ........ *A61N 1/0476* (2013.01); *A61N 1/36021* (2013.01); *A61N 1/0408* (2013.01)

(58) Field of Classification Search
USPC .......................................................... 607/152
See application file for complete search history.

(56) References Cited

U.S. PATENT DOCUMENTS

| | | | |
|---|---|---|---|
| 3,502,076 A | 3/1970 | Bertolini | |
| 3,955,583 A | 5/1976 | Horauf | |
| 4,055,190 A | 10/1977 | Tany et al. | |
| 4,109,660 A | 8/1978 | Nesmeyanov et al. | |
| 4,147,171 A | 4/1979 | Greene et al. | |
| 4,153,060 A | 5/1979 | Korostoff et al. | |
| 4,177,819 A | 12/1979 | Kofsky et al. | |
| 4,244,373 A | 1/1981 | Nachman | |
| 4,535,777 A | 8/1985 | Castel | |
| 4,550,733 A | 11/1985 | Liss et al. | |
| 4,553,549 A | 11/1985 | Pope et al. | |
| 4,590,942 A | 5/1986 | Brenman et al. | |
| 4,676,257 A | 6/1987 | Halpern | |
| 4,782,837 A | 11/1988 | Hogan | |
| 4,784,142 A | 11/1988 | Liss et al. | |
| 4,854,865 A | 8/1989 | Beard et al. | |
| 4,924,880 A | 5/1990 | O'Neill et al. | |
| 5,018,525 A | 5/1991 | Konobevtsev et al. | |
| 5,052,391 A | 10/1991 | Silberstone et al. | |
| 5,067,495 A | 11/1991 | Brehm | |
| 5,304,207 A | 4/1994 | Stromer et al. | |
| 5,387,231 A | 2/1995 | Sporer | |
| 5,571,149 A | 11/1996 | Liss et al. | |
| 5,607,461 A | 3/1997 | Lathrop | |
| 5,620,483 A | 4/1997 | Minogue | |
| 5,626,628 A | 5/1997 | Ganansia et al. | |
| 5,974,342 A | 10/1999 | Petrofsky | |
| 6,212,435 B1 | 4/2001 | Lattner et al. | |
| 6,249,706 B1 | 6/2001 | Sobota et al. | |
| 6,595,775 B1 | 7/2003 | Berk et al. | |
| 6,684,639 B2 | 2/2004 | Ichinose et al. | |
| 6,832,912 B2 | 12/2004 | Mao et al. | |
| 7,029,276 B2 | 4/2006 | Mao et al. | |
| 8,165,668 B2 | 4/2012 | Zipfel et al. | |
| 8,602,777 B2 | 12/2013 | Bryce et al. | |
| 8,770,969 B2 | 7/2014 | Abatelli et al. | |
| 8,909,346 B2 | 12/2014 | Chalmers et al. | |
| 8,948,864 B2 | 2/2015 | Colthurst | |
| 9,028,250 B2 | 5/2015 | Lowe et al. | |
| 9,061,148 B2 | 6/2015 | Bachinski et al. | |
| 9,119,963 B1 | 9/2015 | Al-Shemmeri | |
| 9,242,118 B2 | 1/2016 | Brawn | |
| 9,662,183 B2 | 5/2017 | Lowe et al. | |
| 9,855,418 B2 | 1/2018 | Haralambidis | |
| 9,895,539 B1 | 2/2018 | Heit et al. | |
| 11,103,696 B2* | 8/2021 | Haralambidis | A61N 1/0472 |
| 11,191,951 B2* | 12/2021 | Haralambidis | A61C 19/06 |
| 2001/0034544 A1 | 10/2001 | Mo | |
| 2003/0018367 A1 | 1/2003 | Dilorenzo et al. | |
| 2004/0044338 A1 | 3/2004 | Lennox et al. | |
| 2004/0267333 A1 | 12/2004 | Kronberg et al. | |
| 2007/0276449 A1 | 11/2007 | Gunter et al. | |
| 2008/0227046 A1 | 9/2008 | Lowe et al. | |
| 2008/0233541 A1 | 9/2008 | De et al. | |
| 2009/0117513 A1 | 5/2009 | Nemeh et al. | |
| 2010/0055634 A1 | 3/2010 | Spaulding et al. | |
| 2010/0312233 A1 | 12/2010 | Furnish et al. | |
| 2012/0148975 A1 | 6/2012 | Brawn et al. | |
| 2013/0013028 A1 | 1/2013 | Kriksunov et al. | |
| 2013/0066394 A1 | 3/2013 | Saab et al. | |
| 2013/0085551 A1 | 4/2013 | Bachinski et al. | |
| 2013/0196284 A1 | 8/2013 | Brawn et al. | |
| 2013/0209964 A1 | 8/2013 | Nemeh et al. | |
| 2013/0280671 A1 | 10/2013 | Brawn et al. | |
| 2014/0023983 A1 | 1/2014 | Lowe et al. | |
| 2014/0072932 A1 | 3/2014 | Brawn et al. | |
| 2014/0081256 A1 | 3/2014 | Carmel et al. | |
| 2014/0194946 A1 | 7/2014 | Thomas et al. | |
| 2014/0194949 A1 | 7/2014 | Wichner et al. | |
| 2014/0277323 A1 | 9/2014 | Tingey | |
| 2014/0316310 A1 | 10/2014 | Ackermann et al. | |
| 2016/0001082 A1 | 1/2016 | Butera et al. | |
| 2016/0022989 A1 | 1/2016 | Pfeifer | |
| 2016/0045731 A1 | 2/2016 | Simon et al. | |
| 2016/0325092 A1 | 11/2016 | Haralambidis | |
| 2018/0104476 A1 | 4/2018 | Haralambidis | |
| 2018/0369566 A1 | 12/2018 | Wainless et al. | |
| 2019/0117961 A1 | 4/2019 | Haralambidis | |
| 2019/0366075 A1 | 12/2019 | Haralambidis | |

FOREIGN PATENT DOCUMENTS

| | | |
|---|---|---|
| CN | 101203186 A | 6/2008 |
| CN | 102438698 A | 5/2012 |
| CN | 103458823 A | 12/2013 |
| CN | 107847742 B | 9/2021 |
| EP | 1525857 A1 | 4/2005 |
| EP | 2218477 A1 | 8/2010 |
| EP | 2384664 B1 | 2/2014 |
| EP | 3291880 A1 | 3/2018 |
| JP | 6860503 B2 | 3/2021 |
| KR | 20030070226 A | 8/2003 |
| WO | 01/003768 A1 | 1/2001 |
| WO | 2005077452 A1 | 8/2005 |
| WO | 2008145724 A1 | 12/2008 |
| WO | 2010103263 A1 | 9/2010 |
| WO | 2016179363 A1 | 11/2016 |
| WO | 2018099770 A1 | 6/2018 |
| WO | 2020123732 A2 | 6/2020 |

OTHER PUBLICATIONS

"Examination Report Received for Canada Patent Application No. 2999710, dated Apr. 5, 2022.", dated Apr. 5, 2022, 5 Pages.

Japan Patent Office, "Notice of Allowance Received", Japanese Patent Application No. 2017-558378, dated Mar. 12, 2021, 5 Pages.

U.S. Patent and Trademark Office, "Corrected Notice of Allowability Received", U.S. Appl. No. 16/540,112, dated Aug. 23, 2021, 8 Pages.

U.S. Patent and Trademark Office, "Non-Final Office Action Received", U.S. Appl. No. 16/540,112, dated Apr. 5, 2021, 5 Pages.

U.S. Patent and Trademark Office, "Non-Final Office Action Received", U.S. Appl. No. 16/220,519, dated Jun. 2, 2020, 5 Pages.

U.S. Patent and Trademark Office, "Notice of Allowance Received", U.S. Appl. No. 16/540,112, dated Aug. 11, 2021, 11 Pages.

U.S. Patent and Trademark Office, "Notice of Allowance Received", U.S. Appl. No. 16/220,519, dated Apr. 6, 2021, 7 Pages.

U.S. Patent and Trademark Office, "Notice of Allowance Received", U.S. Appl. No. 16/220,519, dated Dec. 14, 2020, 7 Pages.

Abd-Elmeguid, et al., "Dental Pulp Neurophysiology: Part 1. Clinical and Diagnostic Implications", Jcda, url: www.cda-adc.ca/jcda, vol. 75, No. 1, Feb. 2009, pp. 55-59.

Ackermann, Jr., et al., "Conduction Block of Peripheral Nerve Using High Frequency Alternating Currents Delivered through an Intrafascicular Electrode", Muscle Nerve., vol. 41, No. 1, Jan. 2010, 5 Pages.

(56) References Cited

OTHER PUBLICATIONS

Ackermann, Jr., et al., "Effect of Bipolar Cuff Electrode Design on Block Thresholds in High-Frequency Electrical Neural Conduction Block", IEEE Trans Neural Syst Rehabil Eng., vol. 17, No. 5, Oct. 2009, 22 pages.

Allard, et al., "Voltage-gated Sodium Channels Confer Excitability to Human Odontoblasts", Possible Role in Tooth Pain Transmission, The Journal of Biological Chemistry, vol. 281, No. 29, Sep. 29, 2006, pp. 29002-29010.

Alvarez-Arenal, et al., "Effect of Occlusal Splint and Transcutaneous Electric Nerve Stimulation on the Signs and Symptoms of Temporomandibular Disorders in Patients with Bruxism", Journal of Oral Rehabilitation, vol. 29, 2002, pp. 858-863.

Andersson, et al., "Evaluation of the Pain Suppressive Effect of Different Frequencies of Peripheral Electrical Stimulation in Chronic Pain Conditions", Acta Orthop. Scand., vol. 47, 1976, pp. 149-157.

Asadi, et al., "Bacterial Inhibition by Electrical Stimulation", Department of Physical Therapy, Faculty of Medical Sciences, Tarbiat Modares University, Tehran, Iran, Advances in Wound Care, vol. 3, No. 2., Apr. 14, 2013, pp. 91-97.

Bauer, "Electrical Treatment of Severe Head and Neck Cancer Pain", Arch Otolaryngol—vol. 109, Jun. 1983, pp. 382-383.

Bhadra, et al., "Block of Mammalian Motor Nerve Conduction Using High Frequency Alternating Current", 10th Annual Conference of the International FES Society, Montreal, Canada, Jul. 2005, 3 Pages.

Bhadra, et al., "High Frequency Electrical Conduction Block of the Pudendal Nerve", J Neural Eng, vol. 3, No. 2, Jun. 2006, 14 Pages.

Burstone, et al., "Beta Titanium: A New Orthodontic Alloy", American Journal of Orthodontics, vol. 77, No. 2, Feb. 1980, pp. 121-132.

Cassanelli, et al., "Alteration of Membrane Permeability of Bacteria and Yeast by High Frequency Alternating Current (HFAC)", The Open Microbiology Journal, 2008, vol. 2, Apr. 15, 2008, pp. 32-37.

Chinese Patent Office, "First Office Action Received", China Application No. 201680039999.8, dated Jul. 29, 2020, 19 Pages.

European Patent Office, "Communication under Rule 71(3) Received", European Application No. 16790069.5, dated Dec. 19, 2019, 6 Pages.

European Patent Office, "Extended European Search Report", European Application No. 16790069.5, dated Dec. 13, 2018, 12 Pages.

Frankstein, "One Unconsidered Form of the Part Played by the Nervous System in the Development of Disease", Science, Downloaded from http://science.sciencemag.org/, Apr. 10, 2017, 2 Pages.

Han, et al., "Dental Implant Electrical Stimulation Healing Device", Department of Stomatology, the Chinese PLA general hospital Beijing, China, International Conference on Materials, Manufacturing and Mechanical Engineering (MMME 2016), Dec. 30-31, 2016, pp. 83-86.

Hansson, et al., "Transcutaneous Electrical Nerve Stimulation (TENS) as Compared to Placebo TENS for the Relief of Acute Oro-Facial Pain", Pain, vol. 15, No. 2, 1983, Elsevier Biomedical Press, Mar. 24, 1982, pp. 157-165.

Hughes, Jr., et al., "Response of Plasma beta-Endorphins to Transcutaneous Electrical Nerve Stimulations in Healthy Subjects", Physical Therapy, vol. 64, No. 7, Jul. 1984, pp. 1062-1066.

Japan Patent Office, "Office Action Received", Japan Application No. 2017-558378, dated Apr. 27, 2020, 7 Pages.

Kilgore, et al., "Reversible Nerve Conduction Block Using Kilohertz Frequency Alternating Current", Neuromodulation, vol. 17, No. 3, Apr. 2014, 32 Pages.

Kuzyk, et al., "The Science of Electrical Stimulation Therapy for Fracture Healing", Indian Journal of Orthopedics, Apr.-Jun. 2009, vol. 43, No. 2, Mar. 30, 2017, 12 Pages.

Long, "Electrical Stimulation for the Control of Pain", Aech Surg, vol. 122, Jul. 1977, Apr. 11, 2017, pp. 884-888.

McCullen, et al., "Application of Low-Frequency Alternating Current Electric Fields Via Interdigitated Electrodes: Effects on Cellular Viability, Cytoplasmic Calcium, and Osteogenic Differentiation of Human Adipose-Derived Stem Cells", Tissue Engineering: Part C, vol. 16, No. 6, 2010, pp. 1377-1386.

Melzack, et al., "Pain Mechanisms: A new Theory", Science, vol. 150, No. 3699, Nov. 19, 1965, pp. 971-979.

Melzack, "Prolonged Relief of pain by Brief, Intense Transcutaneous Somatic Stimulation", Pain, vol. 1, No. 4, Dec. 1975, pp. 357-373.

Mirzaii, "Antibacterial Effect of Alternating Current Against *Staphylococcus aureus* and Pseudomonas Aeroginosa", ISSN 2304-3415, Russian Open Medical Journal, vol. 4., No. 2, Article CID e0203, Mar. 20, 2015, 5 Pages.

Patel, et al., "Differential Fiber-Specific Block of Nerve Conduction in Mammalian Peripheral Nerves Using Kilohertz Electrical Stimulation", Innovative Methodology, J Neurophysiol, vol. 113, Apr. 15, 2015, pp. 3923-3929.

Petrofsky, et al., "Effect of Electrical Stimulation on Bacterial Growth", 21 Pages.

Roth, et al., "Effect of transcutaneous electrical nerve stimulation for controlling pain associated with orthodontic tooth movement", Am. J. Orthod. Dentofac. Orthop., vol. 90, No. 2, Aug. 1986, pp. 132-138.

Russian Fedration, "International Search Report and Written Opinion Received", Application No. PCT/US2016/030922, dated Sep. 8, 2016, 9 Pages.

Spadari, et al., "Electrical Stimulation Enhances Tissue Reorganization During Orthodontic Tooth Movement in Rats", Clin Oral Invest, Springer-Verlag Berlin Heidelberg, Feb. 26, 2016, 10 Pages.

Stratton, "Role of Endorphins in Pain Modulation", The Journal of Orthopaedic and Sports Physical Therapy, vol. 3, No. 4, Mar. 24, 2017, pp. 200-205.

U.S. Patent and Trademark Office, "International Search Report and Written Opinion", PCT Application No. PCT/US2019/065839, dated Jul. 15, 2020, 14 Pages.

U.S. Patent and Trademark Office, "Non-Final Office Action Received", U.S. Appl. No. 15/147,234, dated Jan. 27, 2017, 8 Pages.

U.S. Patent and Trademark Office, "Non-Final Office Action Received", U.S. Appl. No. 15/147,234, dated Jun. 27, 2017, 20 Pages.

U.S. Patent and Trademark Office, "Non-Final Office Action Received", U.S. Appl. No. 15/791,462, dated Mar. 29, 2018, 5 Pages.

U.S. Patent and Trademark Office, "Notice of Allowance Received", U.S. Appl. No. 15/791,462, dated Apr. 30, 2019, 7 Pages.

U.S. Patent and Trademark Office, "Notice of Allowance Received", U.S. Appl. No. 15/791,462, dated Dec. 20, 2018, 7 Pages.

U.S. Patent and Trademark Office, "Notice of Allowance Received", U.S. Appl. No. 15/147,234, dated Oct. 19, 2017, 8 Pages.

Wang, "Influence of Frequency and Temperature on the Mechanisms of Nerve Conduction Block Induced by High-Frequency Biphasic Electrical Current", J Comput Neurosci., vol. 24, No. 2,, Apr. 2008, 21 Pages.

Weinberg, "High-Frequency Stimulation of Excitable Cells and Networks", PLoS One, vol. 8, Issue 11, Nov. 2013, 16 Pages.

Weiss, et al., "Transcutaneous Electrical Neural Stimulation for Pain Control", Journal of Clinical Orthodontics, vol. 28, No. 11, 1994, pp. 670-671.

White, "Pain and Cooperation in Orthodontic Treatment", Journal of Clinical Orthodontics, vol. 18, No. 8, 1984, pp. 572-575.

WIPO, "International Preliminary Report on Patentability Received", PCT Application No. PCT/US2016/030922, dated Nov. 16, 2017, 7 Pages.

\* cited by examiner

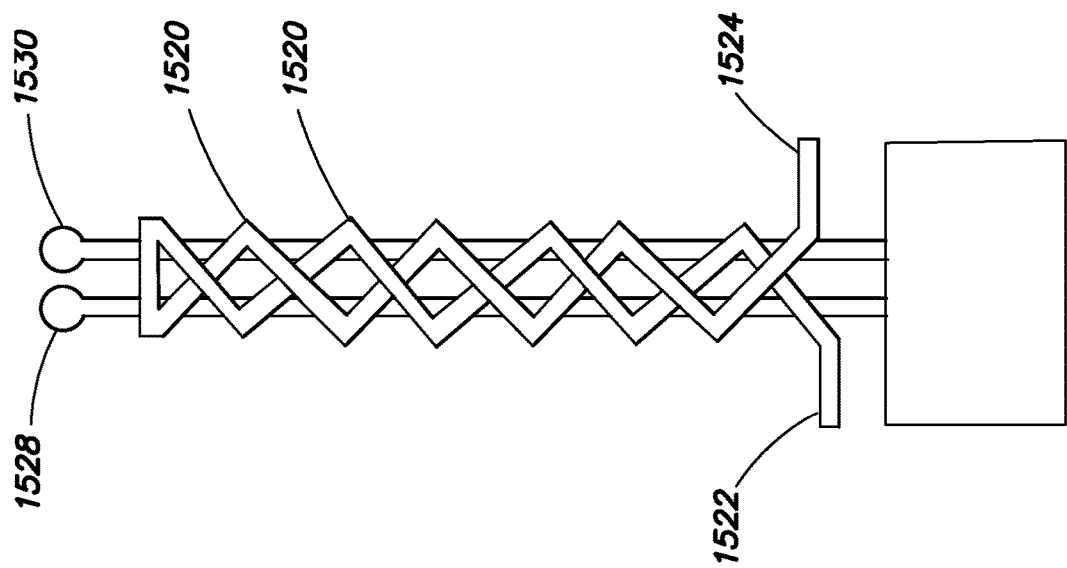
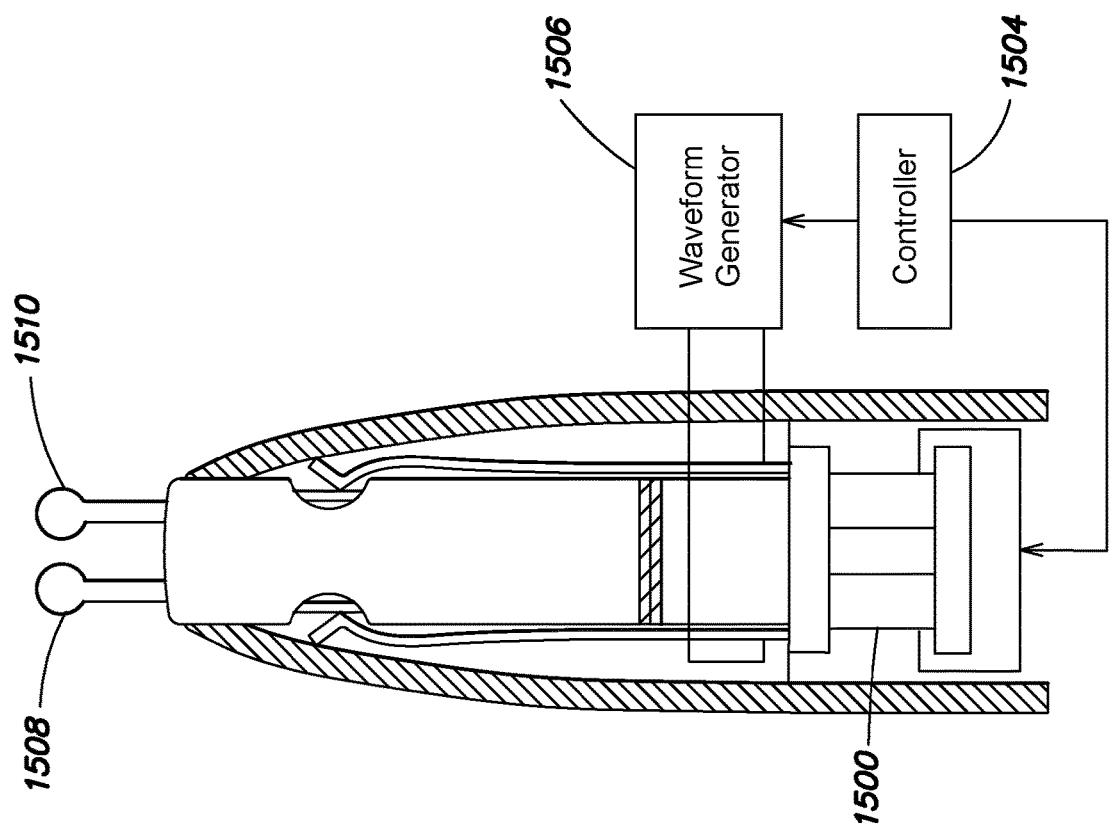

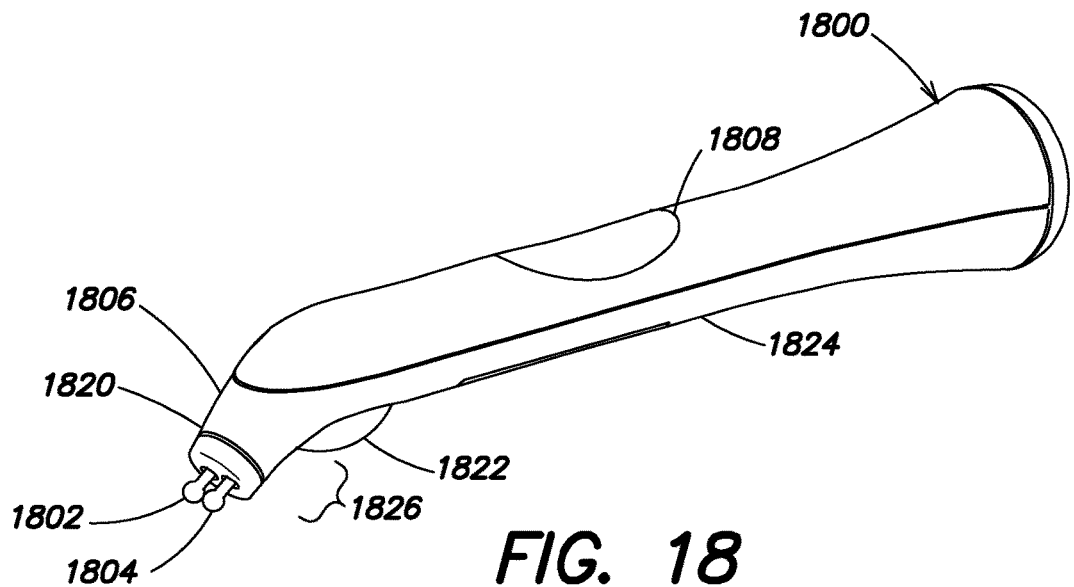
FIG. 18
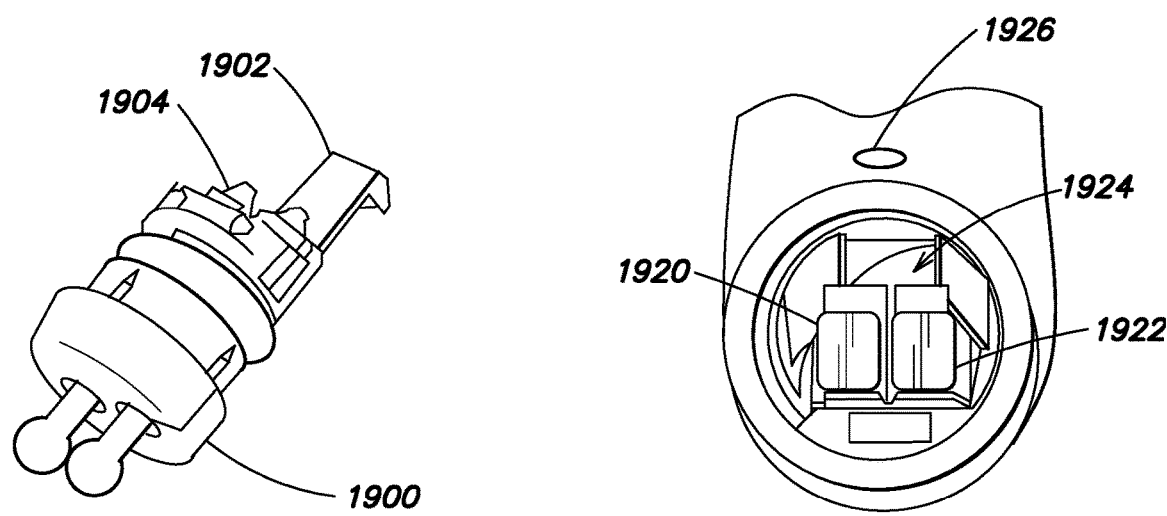
FIG. 19A
FIG. 19B

DEVICE FOR ELECTRICAL STIMULATION OF PERIODONTAL COMPLEX AND SURROUNDING TISSUE

CROSS-REFERENCE TO RELATED APPLICATIONS

This application is a continuation-in-part of U.S. patent application Ser. No. 15/791,462, filed Oct. 24, 2017, pending, which is a continuation of U.S. patent application Ser. No. 15/147,234, filed May 5, 2016, issued as U.S. Pat. No. 9,855,418 on Jan. 2, 2018, which is a nonprovisional application of U.S. Provisional Patent Application 62/157,053, filed May 5, 2015, all of which are hereby incorporated by reference.

BACKGROUND

A significant and common side effect of orthodontic treatment is pain associated with tooth movement. Orthodontic patients experience pain during or immediately following adjustment of an orthodontic appliance, which may last from two to four days. The pain intensity ranges from a slight soreness when clenching to a constant, throbbing pain. Pain associated with orthodontic treatment is due, at least in part, to compression of a highly innervated ligament surrounding a tooth.

There are several manners and techniques used today to alleviate post-adjustment orthodontic pain. Appliances are designed using lighter wires that deliver less force to the teeth. However, many patients continue to report discomfort. Other forms of pain relief come from over the counter pharmacological drugs such as aspirin or other forms of mild analgesics. Side effects are associated with many of these drugs, and these drugs sometimes are not effective.

Another challenge in orthodontic treatment is encouraging tooth movement. The overall duration of orthodontic treatment could be reduced if teeth can be encouraged to move more quickly. There are several manners and techniques used today to attempt to encourage tooth movement, such as appliances that apply light or vibration.

There are other kinds of pain patients experience due to conditions in the mouth, such as canker sores, dental pain due to cavities, infections, and procedures, and endodontic pain. Most forms of relief for such pain are analgesics, antiseptics or numbing agents.

SUMMARY

This Summary introduces selected concepts in simplified form which are described further below in the Detailed Description. This Summary is intended neither to identify essential features, nor to limit the scope, of the claimed subject matter.

A device provides electrical stimulation to one or more components of the periodontal complex and surrounding tissue of a tooth, for uses such as reducing orthodontic or dental pain, encouraging tooth movement, and addressing other conditions of the periodontal complex. The device has electrodes of a rigid, electrically conductive material in a fixed spatial relationship configured for application to oral mucosa and attached gingiva adjacent to, and along a periodontal ligament of, a root structure of a single tooth. An example of such a device is a handheld device with two electrodes which can be placed on a single tooth at a time by a patient, caretaker or care provider. Another example of such a device is an array of pairs of electrodes, shaped for application to multiple teeth, with each pair of electrodes configured to be applied to a different tooth.

With such a device, an electrical circuit is configured for electrical connection to the at least two electrodes. The electrical circuit has an output providing an electrical stimulus comprising a waveform in accordance with predetermined stimulation parameters. After the electrodes are applied to the oral mucosa and attached gingiva adjacent to, and along the periodontal ligament of, a root structure of the tooth, a switch, when activated, activates the electrical circuit to output the electrical stimulus through the at least two electrodes. The electrical circuit and/or the switch can be housed, along with the electrodes, in a single integrated housing, or can connect to a housing containing the electrodes using a variety of electrical and mechanical connections.

In some implementations, the electrical stimulus is designed for the reduction of pain associated with orthodontic tooth movement. In some implementations, the electrical stimulus is designed for the reduction of dental pain due to cavities, infections, or other conditions or procedures. In some implementations, the electrical stimulus is designed for the reduction of endodontic pain due to various conditions or procedures. In some implementations, the electrical stimulus is designed for encouraging cellular activity and healing of soft tissue and ligaments, to increase or decrease speed of tooth movement. In some implementations the electrical stimulus is designed to address other conditions in the mouth, such as canker sores.

In the following description, reference is made to the accompanying drawings which form a part hereof, and in which are shown, by way of illustration, specific example implementations of this technique. It is understood that other embodiments may be utilized, and structural changes may be made without departing from the scope of the disclosure.

BRIEF DESCRIPTION OF THE DRAWINGS

FIGS. 15A and 15B are illustrations of example devices in which thermal stimulus such as cooling is combined with an electrical stimulus.

FIG. 18 is a perspective view of an example implementation of a handheld device.

FIG. 19A is a perspective view of an example construction of electrodes for the device of FIG. 18.

FIG. 19B is a perspective view of an example construction of a tip of a handle of the device into which the electrodes of FIG. 19A connect.

DETAILED DESCRIPTION

The following detailed description sets forth example implementations of a device for electrical stimulation of one or more components of the periodontal complex and surrounding tissue of a tooth, for uses such as reducing orthodontic pain and encouraging tooth movement. The device has electrodes of a rigid, electrically conductive material in a fixed spatial relationship configured for application to oral mucosa and attached gingiva adjacent to, and along a periodontal ligament of, a root structure of a single tooth. An electrical circuit applies, through the electrodes, a subsensory or slightly sensory electrical stimulus comprising a waveform in accordance with predetermined stimulation parameters. Examples of such a device described below include a handheld device with two electrodes which can be placed on a single tooth at a time by a patient, caretaker or care provider. Another example of such a device is an array of pairs of electrodes, shaped for application to multiple teeth, with each pair of electrodes applied to a different tooth.

A first example implementation of such a device will now be described in connection with FIGS. 1-3. Additional configurations are shown in FIGS. 18 and 19. A second example implementation of such a device is described below in connection with FIGS. 8-13. An example implementation of an electrical circuit that can be used in either implementation is described below in connection with FIGS. 4A and 4B through 6. Additional embodiments are shown in FIGS. 14 through 17. A flowchart describing an example treatment process using either device is described below in connection with FIG. 7.

Figure 1:
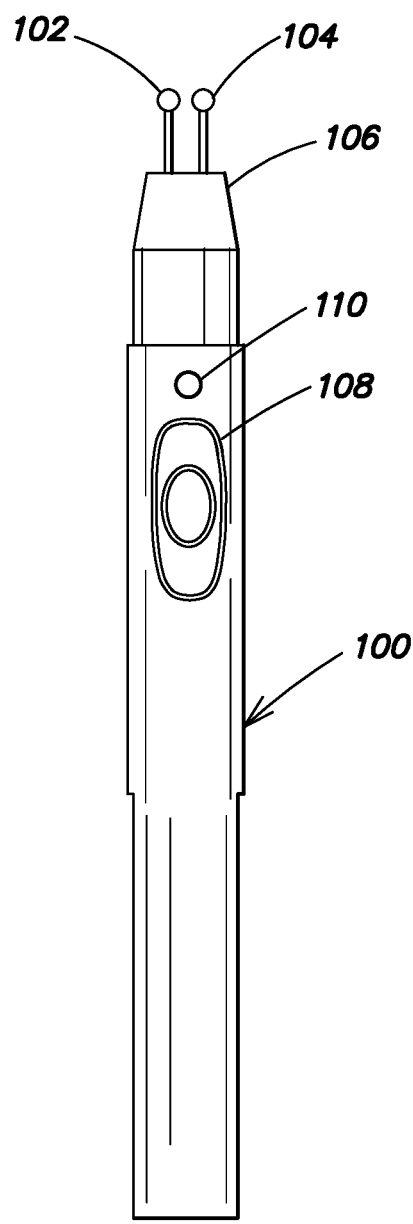
FIG. 1 is a perspective view of an example implementation of a handheld device for electrical stimulation a periodontal complex and surrounding tissue of a tooth.
Figure 4A:
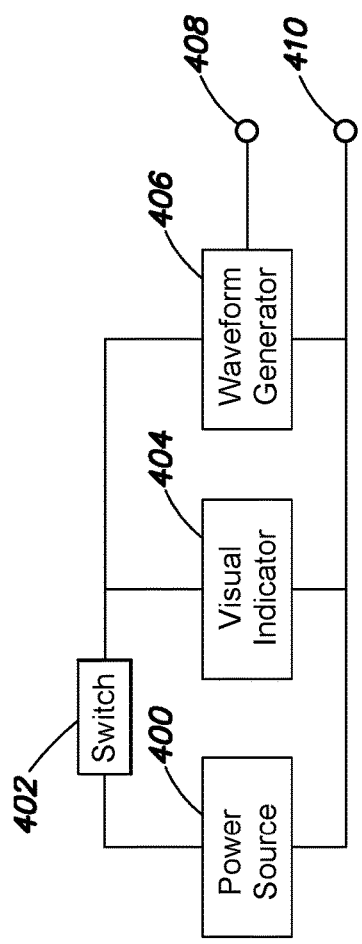
FIG. 4A is a block diagram of an example implementation of an electrical circuit that generates an electrical stimulus.
Figure 4B:
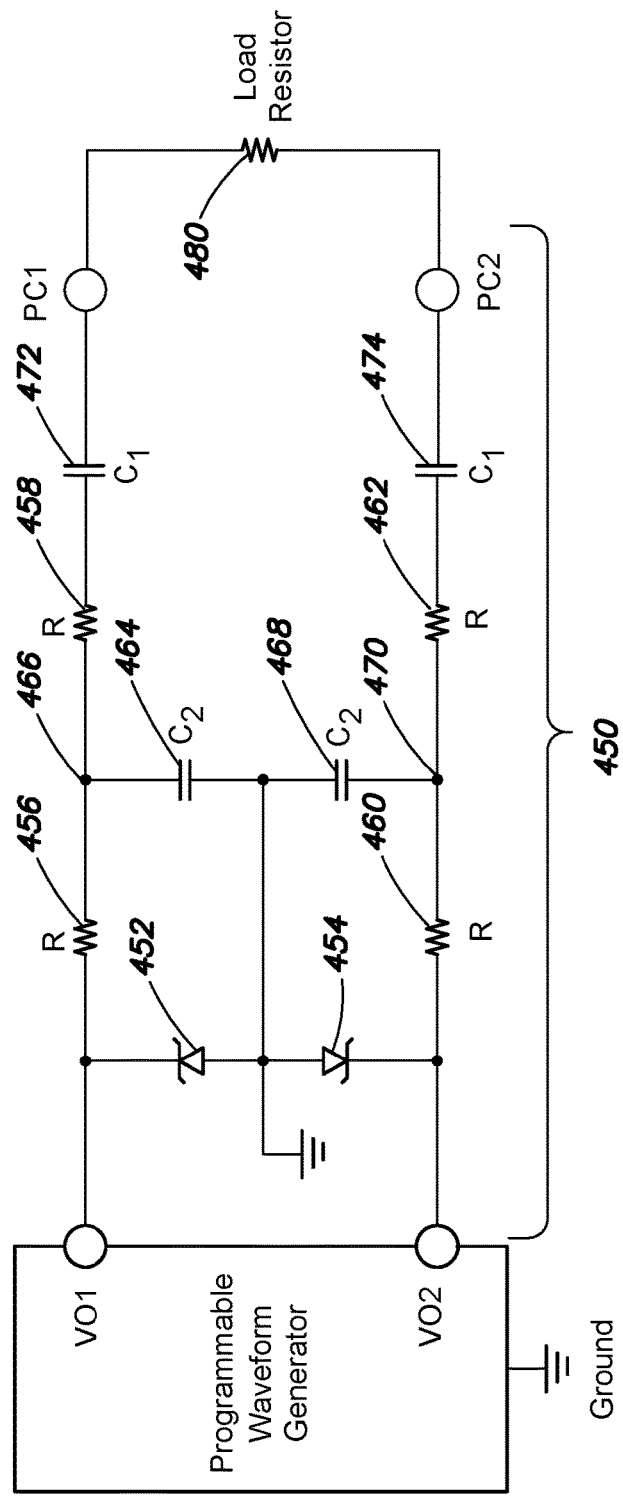
FIG. 4B is a circuit diagram of an example implementation of the electrical circuit of FIG. 4A.

In FIG. 1, a device for electrical stimulation of the periodontal complex and surrounding tissue of a tooth includes a housing 100 configured to be handheld. At least two electrodes 102, 104 of a rigid, electrically conductive material and in a fixed spatial relationship are mounted at a first end 106 of the housing. With this example implementation, when the device is used, the electrodes of the device are manually placed on a desired location in the mouth. An electrical circuit (not shown in FIG. 1), such as described in more detail below in connection with FIGS. 4A and 4B, is electrically connected to the at least two electrodes 102, 104. The electrical circuit has an output providing, through the at least two electrodes, a subsensory electrical stimulus comprising a waveform in accordance with predetermined stimulation parameters. A switch 108 is provided which can be manipulated by a user to activate the electrical circuit to initiate the output of the electrical stimulus through the at least two electrodes 102, 104.

The electrical circuit and/or the switch can be housed in the housing 100 with the electrodes, as shown in FIG. 1, or can connect to a housing containing the electrodes using a variety of electrical and mechanical connections. The housing can also contain a battery or can be configured to accept an external power source through an appropriate electromechanical connection. The housing can be made of, for example, an acrylic or suitable plastic, or other solid material commonly used for similar devices. The housing can have a mating cap (not shown) to cover the electrodes when not in use.

As shown in this example implementation, a light 110, such as a light emitting diode, or other visible element, can be provided on the housing. When the electrical circuit is activated and is outputting the electrical stimulus, the light can be used to indicate operation of the device. Such a light also can be configured with the electrical circuit to indicate adequate battery power.

Figure 2:
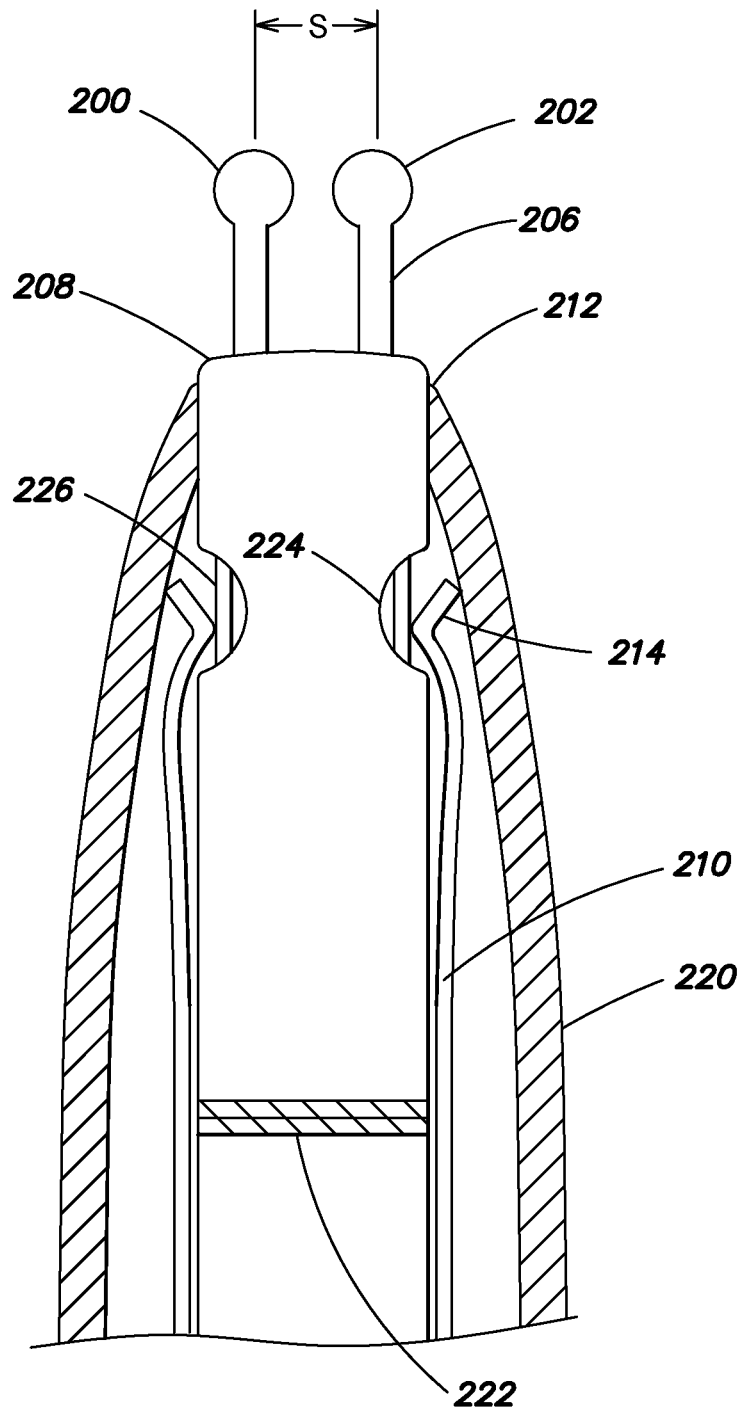
FIG. 2 is a perspective view of an example construction of electrodes for the device of FIG. 1.

In one example implementation, shown in more detail in FIG. 2, the at least two electrodes comprises two posts 206 of a rigid, electrically conductive material, such as stainless steel, connected to a base 208. While the posts 206 are illustrated as being straight, the posts can be angled to improve the ability of an operator of the device to reach teeth in the back of the mouth. The electrodes are rigid in the sense that the electrodes retain their shape and position without an external force; however, the electrodes can be made of a material than can be manipulated, shaped or bent. Several metals, such as stainless steel, are suitable for this purpose. The base can be made of ceramic or other insulating material. A tip of each post 206 can be terminated by a sphere 200, 202 of an electrically conductive material, such as stainless steel. The sphere and post of an electrode are preferably made of the same material as a single, integrated piece. Other shapes may be used for the tips, such as flat paddles, rounded tips, or other shapes. The tip size also may vary among applications. The differences in size, shape and number of probes can affect the current density. For example, a larger tip area may be used to apply an initial high current blast, and then a smaller tip area may be used for remaining subsequent stimuli.

While the Figures illustrate two electrodes it should be understood that at least two electrodes encompass more than two electrodes or probe contacts applied to a tooth. There can be any number of probe contacts applied to a tooth. The probe contacts can be configured to be applied to both sides of a tooth. Different numbers and configurations of probe contacts depend on the nerve bundles intended to be affected by the stimulus. Multiple contacts also may result in an effect of the stimulus being achieved more quickly.

The tips of the electrodes are in a fixed spatial relationship, as indicated by spacing "S", which is based on the application of the electrodes to oral mucosa and attached gingiva adjacent to, and along a periodontal ligament of, a root structure of a single tooth, as described in more detail below in connection with FIG. 3. Thus, the spacing of the electrodes is such that they can span an adequate length along the periodontal ligament between the attached gingiva and the oral mucosa. For example, the spacing can be at least two millimeters. As another example, the spacing can be at least three millimeters. As another example, the spacing can be between two millimeters and six millimeters. As another example, the spacing can be between three and five millimeters. As another example, the spacing can be between 3.5 and 4.5 millimeters. As another example the spacing can be approximately four millimeters. In an example implementation as shown, each sphere can be 0.0945 inches or 2.41 mm in diameter, placed about 0.156 inches or 3.98 mm center-to-center apart.

The base 208 can have a shape corresponding to an opening 212 formed at the end of the housing 220, with the opening having a bottom portion 222, and the base 208 can be configured to be removable. With such a construction, the base has a first mechanical connector having a mating configuration with a second mechanical connector of the housing; the base also has a first electrical connection having a mating configuration with a second electrical connection of the housing. Such a construction of the housing and electrode interconnection allows for removal of the electrodes for cleaning or sterilization, for replacement, or to allow various configurations of electrodes to be used.

In the example shown in FIG. 2, the base can engage electrically conductive connectors, e.g., 210, which provide for mechanical engagement of the base 208 with the housing 220, and an electrical connection to a circuit (not shown in FIG. 2) within the housing. The circuit within the housing provides for the electrical connection to the electrical circuit that generates the electrical stimulus. More particularly, in the example shown in FIG. 2, a bent portion 214 of the connector 210 engages an area of the base 208 that forms a gap 224 to provide mechanical engagement; the bent portion 214 also contacts a portion 226 of the post 206 to provide the electrical connection.

Another implementation of a handheld device is shown in FIGS. 18 and 19. In this example, a housing 1800 is configured to be handheld. At least two electrodes 1802, 1804 of a rigid, electrically conductive material and in a fixed spatial relationship are mounted in a tip base 1820 at a first end 1806 of the housing. With this example implementation, when the device is used, the electrodes of the device are manually placed on a desired location in the mouth. An electrical circuit (not shown in FIG. 18), such as described in more detail below in connection with FIGS. 4A and 4B, is electrically connected to the at least two electrodes 1802, 1804. The electrical circuit has an output providing, through the at least two electrodes, an electrical stimulus comprising a waveform in accordance with predetermined stimulation parameters. A switch 1808 can be provided which can be manipulated by a user to activate the electrical circuit to initiate the output of the electrical stimulus through the at least two electrodes 1802, 1804.

Figure 16:
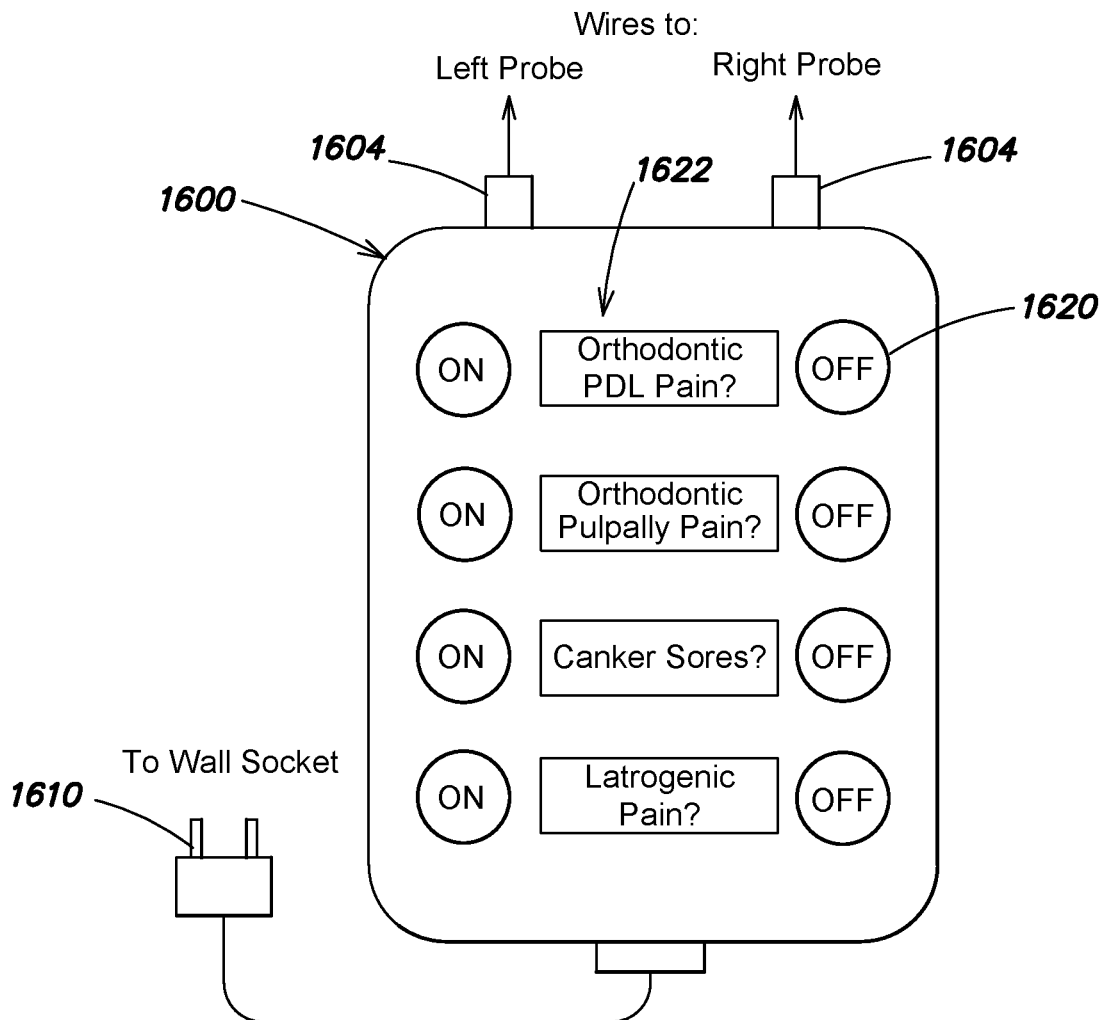
FIG. 16 is an example implementation of a control unit for a device in a tabletop embodiment.
Figure 17:
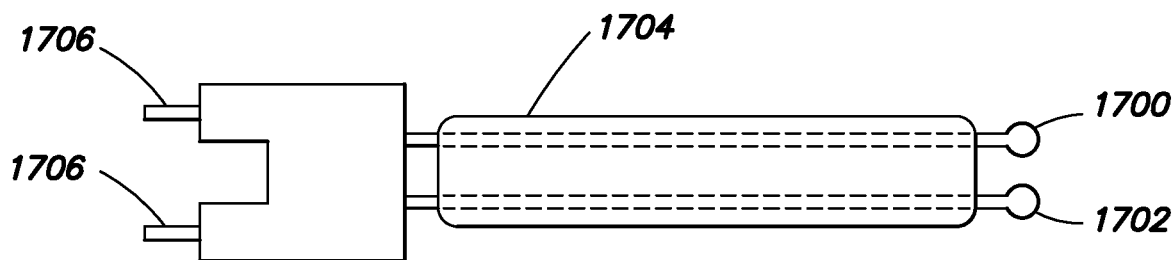
FIG. 17 is an example implementation of a handle of the device in the tabletop embodiment.

The electrical circuit and/or the switch can be housed in the housing 1800 with the electrodes as shown in FIG. 18, or can connect to a housing containing the electrodes using a variety of electrical and mechanical connections, an example of which is shown in FIGS. 16 and 17. The housing can also contain a battery, or can be configured to accept an external power source through an appropriate electromechanical connection. The housing can be made of, for example, an acrylic or suitable plastic, or other solid material commonly used for similar devices. The housing can have a mating cap (not shown) to cover the electrodes 1802, 1804 when the device is not in use. The housing 1800 may be angled, as shown at 1822, such that a handle portion 1824 is at an angle to a tip portion 1826. Such an angle of the tip portion can improve the ability of an operator of the device to reach teeth in the back of the mouth.

It should be understood that the size and shape of the housing such as shown in FIGS. 1 and 18 can be different for different applications. The handles can be ergonomically designed for hands of different sizes, such as for children and adults and individuals with disabilities. The handles may have written instructions for use or may be adorned with art or images of characters from the movies or books or other types of drawings that appeal to intended user.

Turning now to FIG. 19A, the tip base 1900 can have a shape corresponding to an opening formed at the end of the housing 1800. The tip base 1900 can be configured to be removable from the housing 1800. As an example of such a construction, the base can have a mechanical connector 1902 having a mating configuration with a corresponding mechanical connector of the housing. The connector 1902 provides a flexible, snap-fit into the housing 1800. The tip base 1900 also has a first electrical connections 1904 having a mating configuration with a corresponding electrical connection of the housing. The corresponding structure of the handle is shown in FIG. 19B. The first electrical connections 1904 make contact with second electrical connections 1920 and 1922. The connector 1902 snap into a mating structure 1924. It can be released be inserting a narrow instrument into hole 1926.

Figure 3:
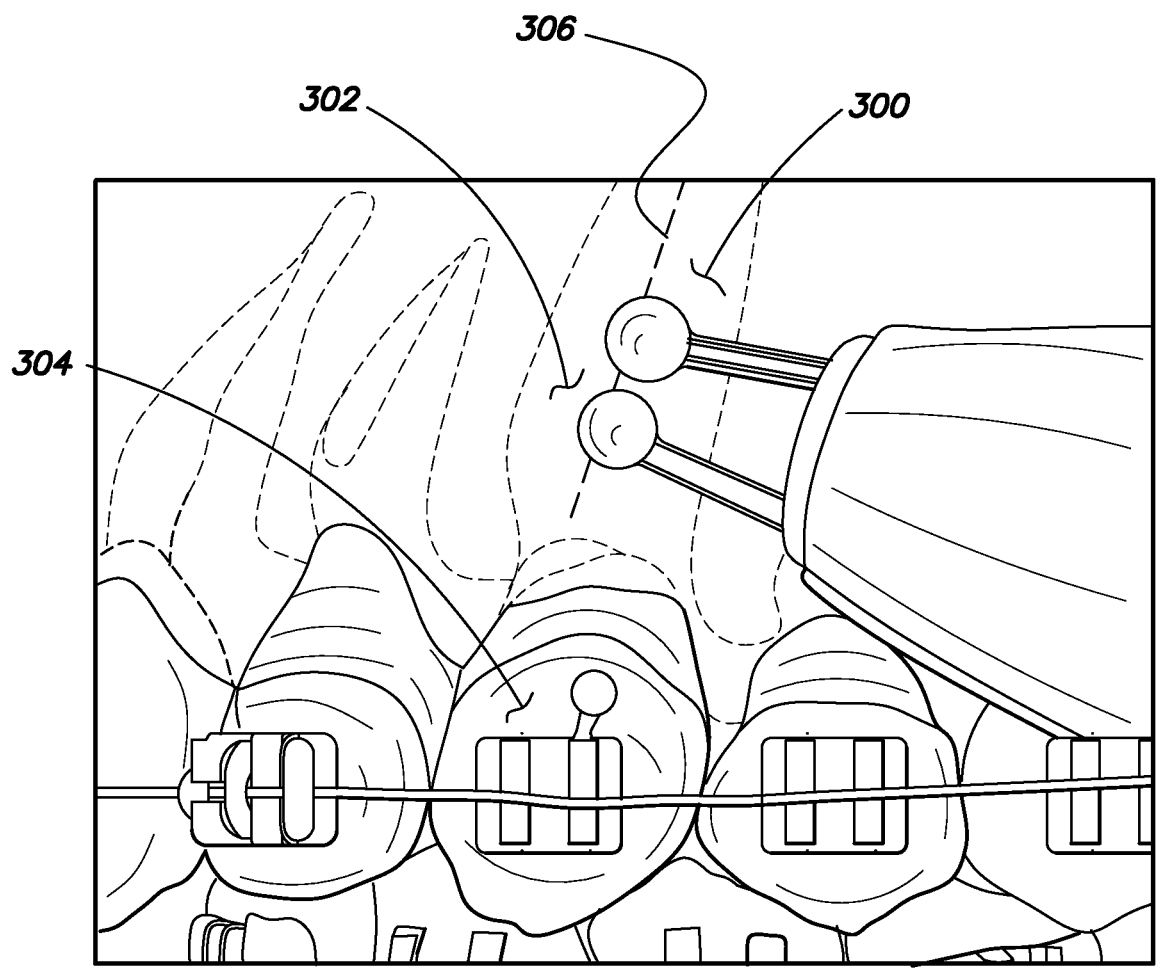
FIG. 3 is a perspective view illustrating electrode placement on oral mucosa and attached gingiva adjacent to, and along a periodontal ligament of, a root structure of a tooth.

Turning now to FIG. 3, placement of the electrodes will now be described in more detail. While FIG. 3 illustrates application of the electrodes to a facial surface, the electrodes can be placed on any surface of the tissue surrounding the periodontal complex, whether facial, palatal, lingual or buccal surfaces. In use, the two electrodes are placed on oral mucosa 300 and attached gingiva 302 adjacent to, and along (as indicated by dashed line 306) a periodontal ligament of, a root structure of a single tooth 304 or on the tooth enamel itself. When the electrical stimulus is applied from the electrical circuit through the electrodes so placed on a tooth, the device electrically stimulates one or more components of the periodontal complex (which includes the tooth, its root nerve, periodontal ligament, and bone) and its surrounding tissue (including gingiva and oral mucosa) of the tooth. Such direct electrical stimulation of one or more components of the periodontal complex and surrounding tissue of the tooth, which includes both a highly innervated ligament that can become compressed and soft tissue which can be damaged by orthodontic adjustments and tooth movement, can stimulate the various pathways or mechanisms that relate to pain and/or increased cellular activity.

Turning now to FIG. 4A, an example implementation of an electrical circuit will now be described. In FIG. 4A, the electrical circuit includes a power source 400, such as a battery. The battery may be rechargeable. The battery may be removable. As an alternative to, or in addition to, a battery, an external power source can be used. A "battery" can include one or more batteries, such as button cell batteries. In one example implementation, a 4.5-volt direct current source can be provided by three 1.5-volt button cell batteries.

A switch 402 is used to activate the electrical circuit. For example, the switch 402 can represent a button switch such as shown on the device in FIG. 1. The switch 402 can include any of a variety of mechanical switches, an electromechanical switch, or an electrical switch. The switching function can be provided by a control signal from an external controller.

The electrical circuit can include a visual indicator 404, such as a light emitting diode, to indicate whether the electrical circuit is active. The visual indicator also, or alternatively, can be selected, and the electrical circuit can be designed, so as to indicate battery level or other operational state of the device.

The electrical circuit also includes a waveform generator 406. The waveform generator is a circuit that generates an electrical stimulus comprising a waveform in accordance with predetermined stimulation parameters. The output of the waveform generator is applied through electrodes 408 and 410. The design of the electrical circuit is dependent on an output waveform and other stimulation parameters defining the electrical stimulus to be generated for a particular application. The predetermined stimulation parameters include at least a form of the output waveform, a pulse frequency of the waveform, and a current. A duration of the electrical stimulus also can be predetermined. The waveform generator is designed to provide the output waveform according to its specified form and pulse frequency. Given a voltage that powers the electrical circuit (which may be a nominal voltage if a battery is used as a power source), a resistance in series with the output of the waveform generator is selected to provide the desired output current.

An example implementation of a circuit of FIG. 4A is shown in FIG. 4B.

In FIG. 4B, outputs VO1 and VO2 of the programmable waveform generator are provided to the probe contacts PC1 and PC2 through an output circuit 450. The output circuit is designed to ensure that no direct current component is output through the probe contacts PC1 and PC2 to the individual's tissues when in contact with the probe. The circuit includes a first Zener diode 452 connected between ground and the output VO1 and a second Zener diode 454 connected between ground and the output VO2. Four resistors of resistance R are provided. A first resistor 456 connects in series between output VO1 and a second resistor 458. A third resistor 460 connects in series between output VO2 and a fourth resistor 462. A first capacitor 464 connects between the junction 466 of first and second resistors and ground. A second capacitor 468 connects between the junction 470 of first and second resistors and ground. The first and second capacitors have capacitance C2. A third capacitor 472 is connected in series with the second resistor 458 and the probe contact PC1; a fourth capacitor 474 is connected in series with the fourth resistor 462 and the probe contact PC2. The third and fourth capacitors have capacitance C1. For the purpose of modeling the circuit, a load resistor 480 represents the load resistance of the tissue when the probe contacts are applied to the tissue. In one implementation, R=110 Ohms, C2=0.01 microfarads, and C1=10 microfarads. The capacitance C1 contributes to reduction of direct current flowing to the patient's tissue.

By having a device with predetermined stimulation parameters, the electrical stimulus can be ensured to be subsensory, for most patients, and in a form for its desired purpose. With such a configuration, patients can safely use the device.

The duration and/or frequency of application of the electrical stimulus also can be controlled by the electrical circuit. For example, the electrical circuit can include one or more timers (not shown in FIG. 4A or 4B). Such timers can further control activation and deactivation of the electrical circuit so that the electrical circuit outputs the electrical stimulus only for a specified duration. Such timers also can further control activation of the electrical circuit so that it cannot be reactivated until a specified period of time has elapsed. In most applications, the duration of a single application is an amount of time greater than ten seconds and less than twenty minutes.

Generally speaking the electrical stimulus should be subsensory or minimally sensory and therapeutically effective for reducing orthodontic pain and/or encouraging tooth movement. Also the current should be alternating current without a direct current offset so that the net current applied to the body is neutral.

The electrical stimulus is subsensory when the voltage and current applied are sufficiently low that there is little or no sensory perception of the electrical stimulus by the patient. In some cases, a patient may still report feeling a low level of tingling or muscle movement. The electrical stimulus is generally subsensory at a current of less than 10 milliamperes. In some cases, the electrical stimulus is generally less than 60 milliamperes. In some cases, the electrical stimulus is greater than 10 milliamperes and less than 60 milliamperes.

The electrical stimulus is therapeutically effective depending on the biological mechanism by which analgesia is produced or by which cellular response is stimulated. While research has demonstrated that such effects occur in humans in response to certain electrical stimuli, the precise biological mechanisms through which analgesic effects or cellular activity occurs in response to electrical stimulation is not well known. In some cases, A-delta and A-beta fibers may be stimulated to block transmission of painful stimuli by small unmyelinated C-fibers in the spinal cord. A-beta fibers appear to be best stimulated at a frequency in the range of about 80 Hz to 130 Hz; A-delta fibers appear to be best stimulated at a frequency in the range of about 2 Hz to 10 Hz, and more particularly 2 Hz to 5 Hz. Both types of fibers also appear to be stimulated with a burst mode high frequency (e.g., greater than 100 Hz) signal interrupted at a rate of about two to three bursts per second. In some cases, an endorphin mediated mechanism may be activated by the electrical stimulus. Yet other biological mechanisms may be affected by electrical stimulation, such as prevention of formation of neural pathways which may otherwise form in response to pain in the absence of such electrical stimulation.

As a particular example, a waveform with a pulse frequency of less than 200 kHz and greater than 0.5 Hz, applied with a current in the range of 20 microamperes to sixty (60) milliamperes, can be therapeutically effective for pain reduction with an application time of as little as ten seconds up to about several minutes per tooth.

More particularly, the frequency range can be between 100 Hz and 200 kHz. More particularly, the frequency range can be between 1 kHz and 12 kHz. In some cases, the frequency range can be between 12 kHz and 200 kHz. In some cases, the frequency range can be greater than 12 kHz. In some cases, the frequency range can be greater than 1 kHz.

More particularly, the current range can be between 1 milliampere and 60 milliamperes. The current range can be between 1 milliampere and 10 milliamperes. The current range can be between 10 milliampere and 60 milliamperes. More particularly, the current range can be between 5 milliamperes and 10 milliamperes. More particularly, the current range can be between 5 milliamperes and 60 milliamperes. In some cases, the current can be greater than 5 milliamperes. In some cases, the current can be greater than 10 milliamperes. In some cases, the current can be less than 60 milliamperes.

Such an electrical stimulus can be applied whenever a patient senses pain after an orthodontic adjustment. Such treatment typically would be applied once a day only for one to four days after an orthodontic adjustment. Orthodontic patients could receive a treatment immediately following any procedure that may cause discomfort. At such a low level of current, there is no sensory perception, and is safe for a wide range of patients including children.

As another example, for encouraging tooth movement, a waveform with a pulse frequency of less than 12 kHz and greater than 0.5 Hz, with a current of approximately 20 microamperes to 800 microamperes, and more particularly 20 microamperes to 200 microamperes can be therapeutically effective with an application time of between about 10 minutes and 20 minutes, for example about 15 minutes. The effective frequency is dependent on the teeth being moved, because bone density is greater in the mandibular arch than in the maxillary arch. Such an electrical stimulus can be applied several times a day, such as two to four times a day, over a period of several days, such as one to fourteen days. The waveform can stimulate the production of osteoclasts in front of a tooth in the direction of movement and of osteoblasts behind the tooth in the direction of movement, to increase the speed of movement, and can stimulate the transformation of osteoblasts into osteocytes, to decrease the likelihood of tooth movement in the opposite direction.

Figure 5A:
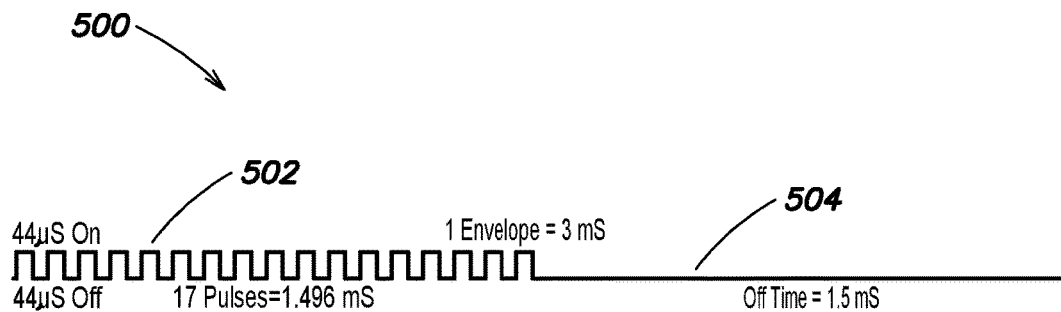
FIG. 5A is an illustration of an example waveform that can be used as an electrical stimulus.
Figure 5B:
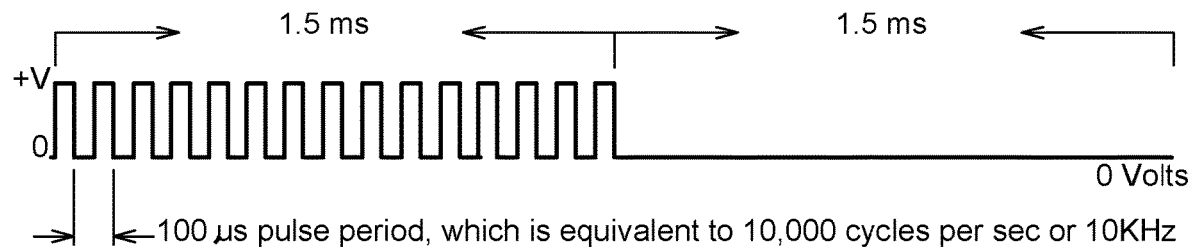
FIG. 5B is an illustration of an example waveform that can be used as an electrical stimulus.
Figure 6:
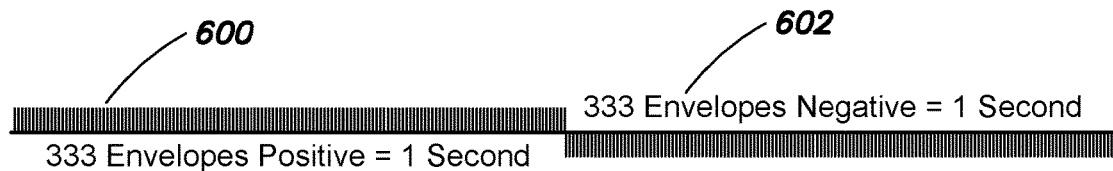
FIG. 6 is a further illustration of the example waveform.

In one implementation, as an example, the electrical stimulus comprises a waveform as shown in FIGS. 5A or FIG. 5B and FIG. 6. In FIG. 5A, this waveform includes a plurality of envelopes, where each envelope 500 includes a plurality of pulses 502 at a pulse frequency, followed by an off time 504. While FIGS. 5A and 5B show the form of the output waveform as a rectangular waveform, pulses can be sloped, e.g., triangular, or curved, e.g., sinusoidal. An envelope can have a positive or negative polarity, i.e., either positive or negative peak voltage. A plurality of such envelopes can be repeated in a sequence, thus providing an envelope frequency.

As a specific example of such a waveform shown in FIG. 5A, pulses of 44 microseconds on followed by 44 microseconds off provide a total pulse width of 88 microseconds, and a pulse frequency of about 11363.6 Hz (11.36 KHz). With 17 such pulses, followed by an off time of 1.5 milliseconds, in one envelope, the envelope time is about three (3) milliseconds, providing an envelope frequency of about 333.3 Hz.

As another specific example of such a waveform shown in FIG. 5B, pulses of 50 microseconds on followed by 50 microseconds off provide a total pulse width of 100 microseconds, and a pulse frequency of about 10 KHz. With 15 such pulses, followed by an off time of 1.5 milliseconds, in one envelope, the envelope time is about three (3) milliseconds, providing an envelope frequency of about 333.3 Hz.

The waveform can include a plurality of envelopes at a first, e.g., positive, polarity, followed a plurality of envelopes at a second, e.g., negative, polarity. Alternating between positive and negative polarity signals provides a net current, when applied to the patient, which is neutral. In the implementation shown in FIG. 6, the waveform includes 333 envelopes 600 at a positive peak voltage, followed by 333 envelopes 602 at a negative peak voltage, to provide one (1) second of a positive signal and one (1) second of a negative signal. The frequency of the positive to negative signal transition is thus 0.5 Hz.

With the waveform such as shown in FIGS. 5A, 5B, and 6, and a nominal battery voltage powering the electrical circuit of about 4.5 volts, and a series resistance of 440 ohms, a nominal maximum output current of about 10 milliamps can be provided.

Considering FIGS. 4B and 5B together, the waveform generator produces a sequence of 333 instances of the basic waveform shown in FIG. 5B, and presents that waveform at output port VO1, while setting output port VO2 to zero volts. This operation consumes one second. After that, the voltage at output port VO1 is then set to zero volts and the 333 envelops of the basic waveform are output at output port V02. This operation consumes one second. The process is repeated for a desired number of seconds. In FIG. 4B, because of the 10 mF series capacitors C1, the voltage seen between probe contacts PC1 and PC2 swings between a negative value and a positive value. The exact voltage shape seen by the load resistors and absolute values depend on the impedance of the load resistor.

Figure 7:
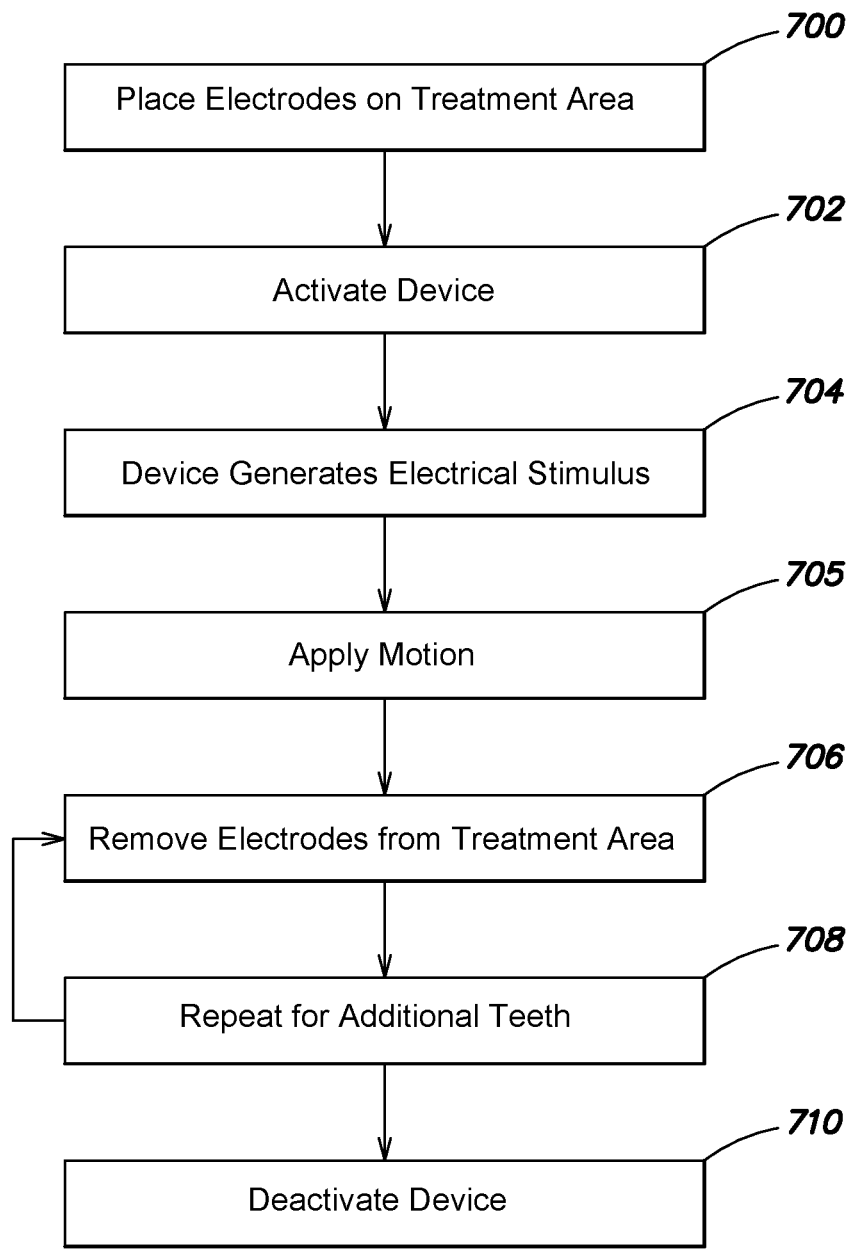
FIG. 7 is a flow chart describing an example process of treatment using such a device.

Turning now to FIG. 7, a flow chart describing an example treatment procedure using such a device will now be described. This treatment process can be performed by an orthodontist or other health care provider, the patient, or a patient's caretaker or parent. Because the device generates a fixed, subsensory (for most patients) or minimally sensory electrical stimulus, this process can even be performed by a child patient.

The electrodes of the device are placed 700 on a treatment area in the mouth, such as shown in FIG. 3. The electrical circuit for the device is activated 702, for example by pressing a button of a device such as shown in FIG. 1, to cause the electrical circuit to generate the desired stimulus. The device generates 704 the stimulus, which is applied through the electrodes to the treatment area. After a period of time, which can be generally about 10 to 60 seconds depending on the condition being treated, the electrodes can be removed 706. During this period of time that the stimulus is being generated and applied to the tooth, the electrodes may be moved 705 about the treatment area. Motion of the electrodes on the treatment area can reduce the likelihood that too much current would be applied in one spot, to reduce the risk of cellular damage, and can increase the area in which treatment is provided and the number of nerve fibers affected by that treatment. The rubbing of the electrodes on the tissue may also activate sensory paths and prepare nerves for stimulus, similar to a rub or pull technique when giving an injection. The electrodes can be placed on another treatment area, as indicated at 708, e.g., by repeating the treatment for additional teeth, to allow the stimulus to be applied to address pain in the other treatment area. When treatment is completed, the device can be deactivated 710. The device may be activated and deactivated between treatments of different treatment areas.

For some orthodontic pain, such as periodontal ligament (PDL) nerve pain, the treatment area is the oral mucosa and attached gingiva adjacent to, and along a periodontal ligament of, a root structure of a single tooth. For this kind of treatment, the electrodes can be moved in a sweeping motion, at a rate of about 5 mm/second. The treatment time is about 20 seconds. An effective amount of time generally is dependent on the tooth size.

For some orthodontic pain, such as pulp-related pain from tooth movement, the treatment area can be on the enamel or dentin of a single tooth, primarily on the center of the coronal cusp. For this kind of treatment, the electrodes generally are held stationary. The treatment time is about 20 seconds. An effective amount of time generally is dependent on the tooth size.

For pain from a canker sore or mouth ulcer or aphthous ulcer or other lesions such as herpetic lesions, the treatment area is the border or edge of the ulcer or lesion. For this kind of treatment, the electrodes can be moved in a sweeping motion, at a rate of about 5 mm/second, around the edge of the ulcer, without making direct contact with the open wound. The treatment time is about 10 to 20 seconds. An effective amount of time generally is dependent on the size of the ulcer.

For some dental pain, such as mild pulpitis, a sensitive exposed root, post-filling sensitivity, post-crown insertion, and pain from a cleaning or polishing, the treatment area can be on the enamel or dentin of a single tooth, primarily on the center of the coronal cusp. For this kind of treatment, the electrodes generally are held stationary on the coronal cusp. The treatment time is about 20 seconds. A treatment area for a secondary application on the same tooth can be at the root apex. For this kind of treatment, the electrodes can be moved in a sweeping motion, at a rate of about 5 mm/second. The treatment time is about 20 seconds. The total treatment time per tooth is about 30 to 60 seconds.

For some dental pain, such as moderate pulpitis, a deep cavity that has not penetrated the pulp, root exposure or recession, temperature sensitivity, and pain from fillings or decay, the treatment area can be on the enamel or dentin of a single tooth, primarily on the center of the coronal cusp. For this kind of treatment, the electrodes generally are held stationary on the coronal cusp. The treatment time is about 20 seconds. A treatment area for a secondary application on the same tooth can be at the root apex. For this kind of treatment, the electrodes can be moved in a sweeping motion, at a rate of about 5 mm/second. The treatment time is about 20 seconds. The total treatment time per tooth is about 30 to 60 seconds.

For pain due to implant surgery or other endodontic pain, the treatment area can be the buccal gingiva, mucosa adjacent the implant, or root area of intact soft issue. For this kind of treatment, the electrodes can be moved in a sweeping motion, at a rate of about 5 mm/second. The treatment time is about 30-60 seconds. If a tooth canal has not been completely de-inervated, direct contact with the enamel or dentin of a single tooth also can be used. For this secondary treatment, the electrodes can be moved in a sweeping motion, at a rate of about 5 mm/second. The treatment time is about 30-60 seconds.

In some applications, the waveform can be fluctuated or changed during the course of treatment. For example, the waveform may be stepped from 5000 Hz to 20,000 Hz, for a set period of time for each frequency, such as several seconds. One reason to fluctuate the frequency is that different nerve bundles may be responsive to different frequencies due to different characteristics of these bundles, such as thicknesses of nerve fibers and myelinated versus unmyelinated.

In some cases, an initial stimulus, followed by a second different stimulus, can be provided for different treatments. Each type of treatment may have a different initial stimulus or a different second stimulus than other treatments. For example, the initial stimulus may be a "silent load" that steadily increases the current so a patient does not "detect" the stimulus. As another example, a "block pulse", with a higher current and/or higher frequency than subsequent pulses may increase potency of an initial pain numbing effect when followed by a steady lower level current with a fluctuating pulse.

Pain relief, stimulation of cellular response, and increased healing rates are not limited to orthodontic treatment. Such a device also can be used to reduce pain and improve healing times for other conditions and/or procedures that affect components of the periodontal complex, such as dental conditions and procedures, endodontic conditions and procedures, implants, and other oral surgery.

Figure 8:
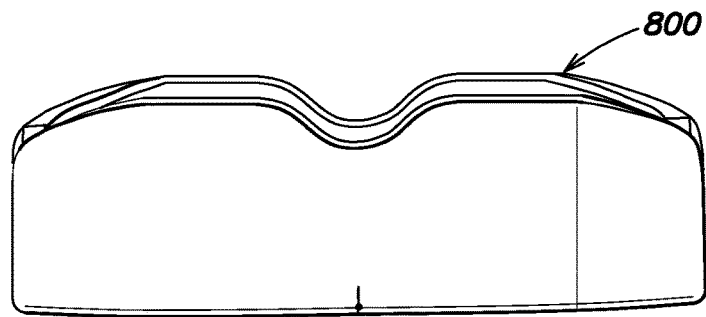
FIG. 8 is front elevation of another example implementation of a device having an array of electrodes.

Referring now to FIGS. 8-13, a second example of an implementation of such a device for electrical stimulation of one or more components of a periodontal complex and surrounding tissue of multiple teeth, will now be described. In this implementation, an array of pairs of electrodes is used to apply electrical stimulation to components the periodontal complexes of multiple teeth. Such an array is particularly useful for encouraging tooth movement throughout the entire mouth, but also can be used for pain reduction. In this device, the principle of electrical stimulation, the stimulation parameters of the electrical stimulus used for treatment, and corresponding electrical circuit for generating the electrical stimulus, are similar to those of a device for treating a single tooth. In FIG. 8, an array of electrodes can deliver the electrical stimulus to multiple teeth. The electrical circuit can be designed to drive all pairs of electrodes simultaneously, or all pairs of electrodes in a subset can be driven simultaneously with each subset being driven in sequence, or individual pairs of electrodes can be driven in sequence, or an individual pair of electrodes can be selected and driven with the electrical stimulus.

Figure 9:
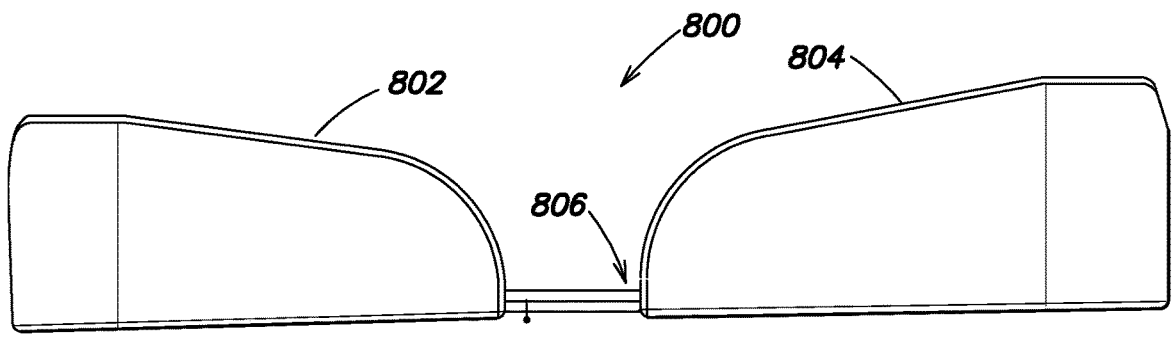
FIG. 9 is a side elevation of the implementation of FIG. 8.
Figure 10:
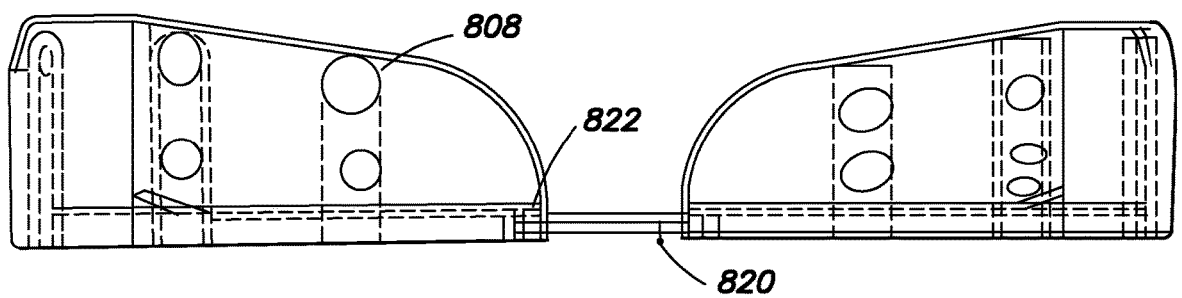
FIG. 10 is a side cross-sectional view of the implementation of FIG. 8.
Figure 11:
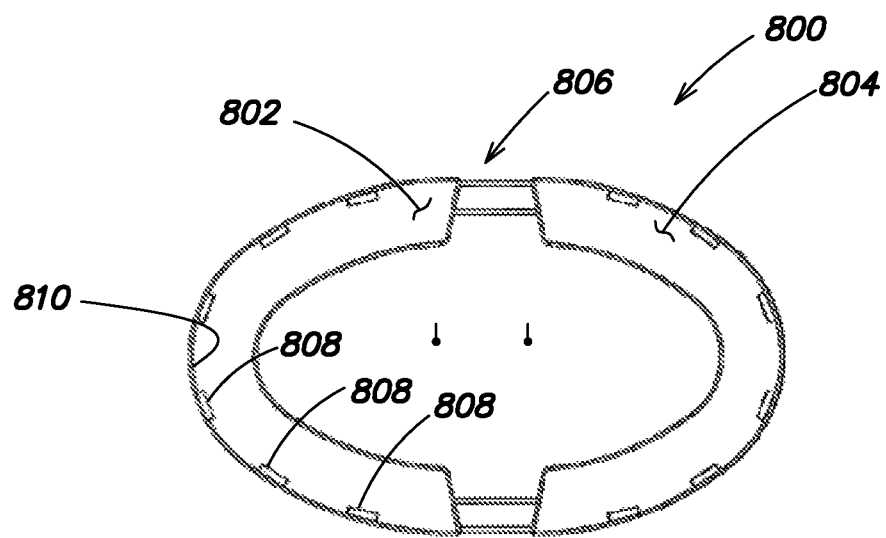
FIG. 11 is a top plan view of the implementation of FIG. 8.
Figure 12:
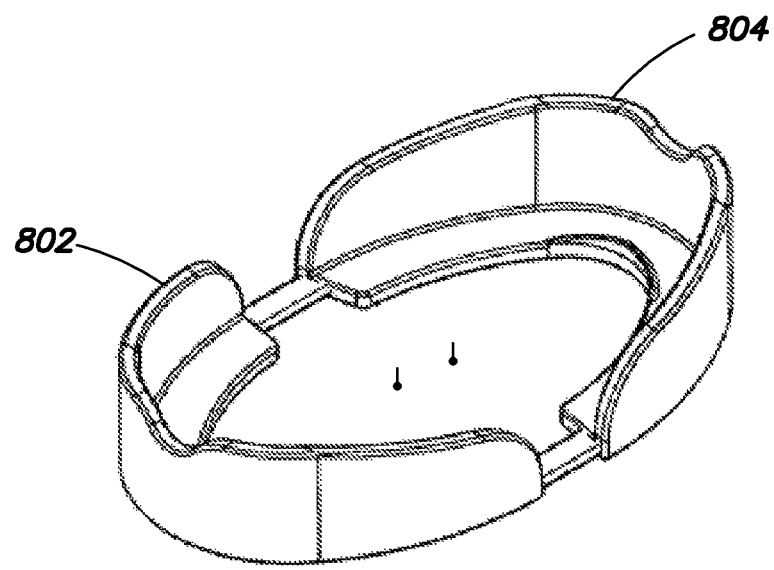
FIG. 12 is a top perspective view of the implementation of FIG. 8.
Figure 13:
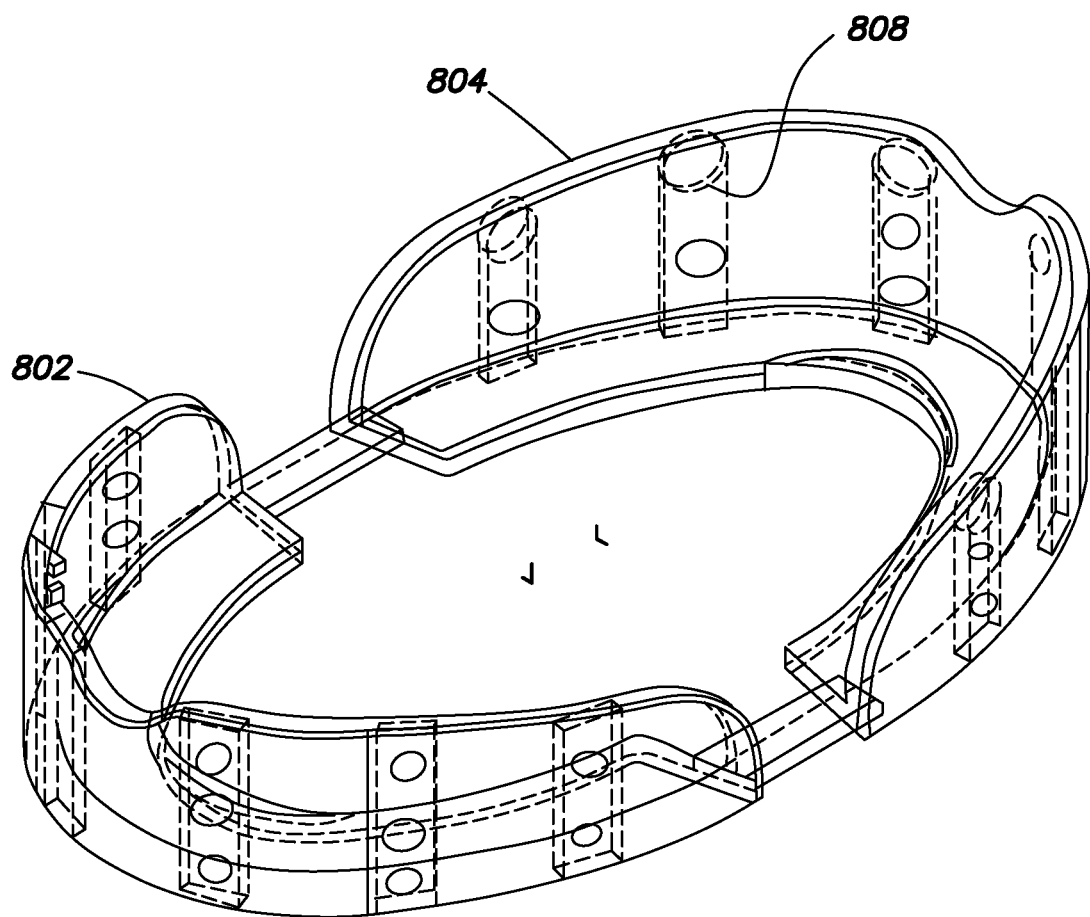
FIG. 13 is a top perspective cross-sectional view of the implementation of FIG. 8

FIG. 8 is front elevation of this example implementation of the device having an array of electrodes. FIG. 9 is a side elevation of the example implementation of FIG. 8. FIG. 10 is a side cross-sectional view of the example implementation of FIG. 8. FIG. 11 is a top plan view of the example implementation of FIG. 8. FIG. 12 is a top perspective view of the example implementation of FIG. 8. FIG. 13 is a top perspective cross-sectional view of the example implementation of FIG. 8.

In this example implementation of the device, a housing 800 is shaped to be placed around teeth along a jaw of a patient. The housing can be designed to encapsulate the electromechanical components in a hermetic package made from biocompatible materials suitable for long term intraoral use. In this example implementation, the housing has a first portion 802 for a top set of teeth, and a second portion 804 for a bottom set of teeth. A flexible portion 806 allows the device to be folded for placement in the mouth. A plurality of pairs 808 of electrodes in a fixed spatial relationship are mounted at locations along an internal face 810 of the housing corresponding to positions of the teeth along the jaw. The electrodes shown in this example implementation are in the form small hemispherical objects of electrically conductive material, such as stainless steel, and having a substantially flat surface facing the soft tissue to which they will be applied. Such electrodes can be about the same size as the spheres shown above in FIG. 2. When the housing is placed in the mouth and surrounding the teeth along the jaw, each pair of electrodes is placed in contact with oral mucosa and attached gingiva adjacent to, and along a periodontal ligament of, a root structure of its corresponding tooth. An electrical circuit, such as shown in FIGS. 4A and 4B, can be connected to the housing 800 through an electromechanical interface 820 and wires 822 (shown in FIG. 10) to deliver the electrical stimulus to the pairs of electrodes. Such a design can be embodied in retainers, an example of which is shown in U.S. Pat. No. 10,098,710, mouthguards and other similar devices.

Figure 14:
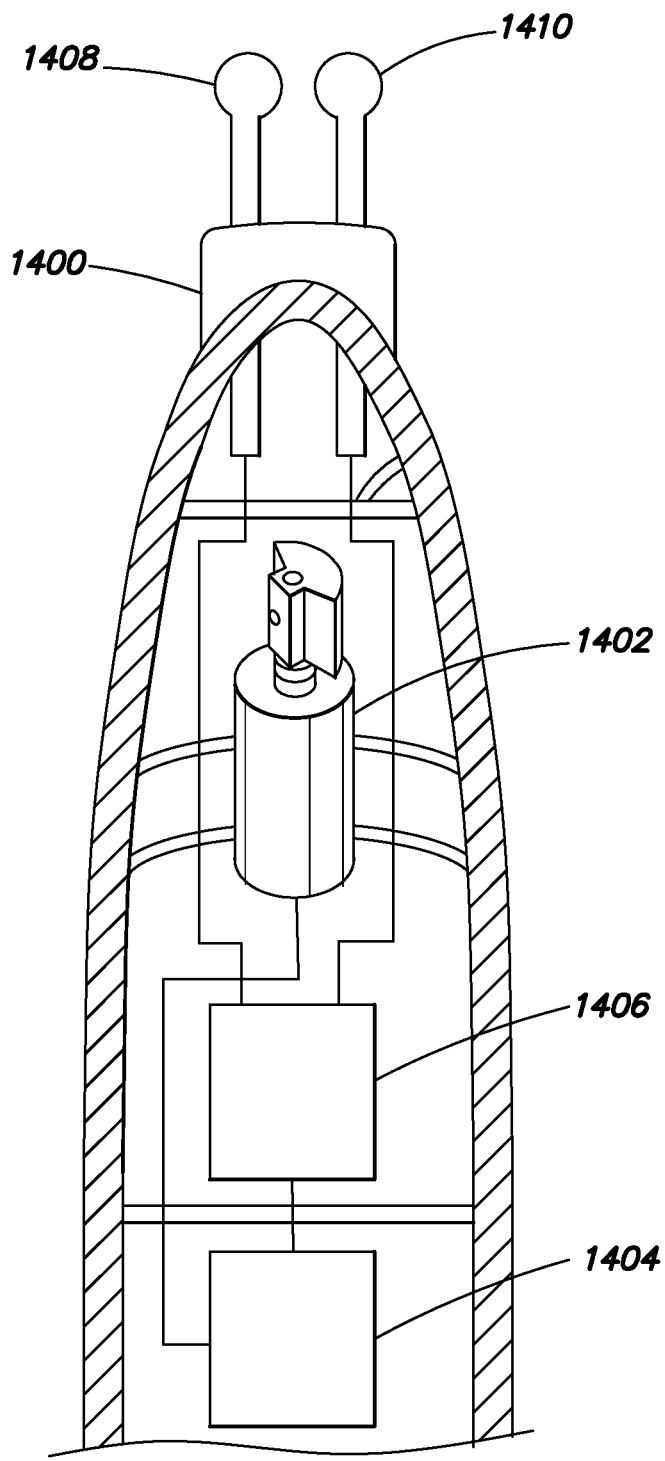
FIG. 14 is an illustration of an example device in which mechanical stimulus such as vibration is combined with an electrical stimulus.

Referring now to FIG. 14, an example device in which mechanical stimulus, such as vibration, is combined with an electrical stimulus will now be described. For example, an electromechanical device can be connected to the electrodes, or the base housing the electrodes, or within the housing of the device. In one implementation, the electromechanical device can be a vibration motor, such as a linear resonant actuator, a housing for the electrodes of the device. In FIG.

14, an example implementation of an electrical circuit includes a waveform generator 1406 that generates the electrical stimulus. A controller 1404 can control operation of the waveform generator and a vibration motor 1402 (shown in slight perspective) which is connected to a housing 1400 for the electrodes of the device. The output of the waveform generator is applied through electrodes 1408 and 1410. A vibration motor 1402 is connected to a housing for the electrodes, and, when activated by the controller 1404, generates a vibration which propagates through the housing to the electrodes.

Referring now to FIGS. 15A and 15B, an example device in which thermal stimulus, such as cooling, is combined with an electrical stimulus will now be described. For example, a thermoelectric device can be connected to one or more of the electrodes. In one implementation, the thermoelectric device can be a solid-state device having two different materials forming a junction capable of exhibiting the Peltier effect. When an electrical current flows in this device across the junction, the device acts as an active heat pump which transfers heat from one side of the device to another side of the device, depending on the direction of the current flow. In FIG. 15A, an example implementation of an electrical circuit includes a waveform generator 1506 that generates the electrical stimulus. The output of the waveform generator is applied through electrodes 1508 and 1510. A thermoelectric device 1500 is connected to the base to cause transfer thermal energy with the tip base and the housing. Another way of providing a thermal stimulus is to heat or cool the electrodes, using any technique typically used for dental or orthodontic applications, prior to applying the electrodes during treatment. Yet another option is to wrap the electrodes 1528, 1530 in a tubing 1520 through which chilled or heated water flows to cool or heat the probe tips as desired, as demonstrated in FIG. 15B. The tubing can have an inlet 1522 into which chilled or heated water or other fluid can flow, and an outlet 1524 from which the fluid can flow. A separate pump (not shown) can be used to cause the fluid to flow, and any conventional thermal system can be used to chill or heat the fluid.

Turning to FIGS. 16 and 17, in this embodiment, the device can be plugged in to a power source, such as a typical outlet in a home or office, using a plug 1610 so there is no need for batteries. Alternatively, the housing 1600 can include replaceable batteries. Such a system includes a control unit (FIG. 16) having a housing 1600 which contains the electronics, and a hand held unit (FIG. 17) which supports the electrodes 1700 and 1702. The electrodes can be encased in a handle 1704, e.g., made of plastic. At one end of the handle, long wires 1706, e.g., about 10 to 20 cm in length or longer, connect to the wires 1604 from the control unit in the housing 1600. A connector (not shown) can be provided anywhere between the housing 1600 and the handle 1704 to allow the handle, and optionally the wires between the handle 1704 and the housing 1600, to be connected to and disconnected from the housing 1600. This housing 1600 could be shaped to allow it to rest on the floor or tabletop or other surface. The housing can have buttons 1620 to allow for selection of different treatment types, for example indicated by labels 1622 on the housing. In response to the user pressing one of the buttons, the circuit is set to generate the corresponding waveform.

In these implementations, the electrodes are separate from the housing containing the electronics. The electrodes could be permanently attached to a short cable which in turn is attached to a longer one that connects to the housing containing the electronics. In this configuration, both the electronics and the electrodes can be made reusable for different patients by being able to autoclave the electrodes and their cables. This is possible if the cables have, as an example, a Teflon coating which is electrically insulating and chemically inert. Autoclave temperature is around 121 degrees C., and Teflon generally retains its integrity up to 250 degrees C.

Such a device also can be configured for long term placement during orthodontic treatment. Electrodes can be placed, and then connected via wires to a device containing the electrical components that generate the desired electrical stimulus.

Other implementations of devices providing electrical stimuli include arrays shaped as a pacifier on which pairs of electrodes are placed at spacings corresponding to individual teeth, such as in an infant's or toddler's mouth. Such a device can help relieve teething or tooth eruption pain of small children.

There are several additional benefits to a patient from using a device such as described herein in connection with orthodontic treatment to electrically stimulate components of the periodontal complex affected by the orthodontic treatment. For example, a reduction in pain experienced by a patient may lead the patient to have better oral hygiene and compliance with other instructions of the orthodontist. Also, many patients may otherwise avoid orthodontic treatment because of pain that is known to be associated with such treatment. The ability to offer more comfortable orthodontic treatment may enable an orthodontist to provide services for previously apprehensive patients. The use of electrical stimulation for pain reduction also may decrease the amount of analgesics consumed by patients. Also, to the extent that electrical stimulation is used in orthodontic treatment to encourage tooth movement and/or tissue growth, such stimulation may improve the healing time associated with tooth movement and may reduce overall treatment time.

It should be understood that the subject matter defined in the appended claims is not necessarily limited to the specific implementations described above. The specific implementations described above are disclosed as examples only.

What is claimed is:

1. A device for electrical stimulation of one or more components of a periodontal complex and surrounding tissue of a tooth, comprising:
    at least two electrodes of a rigid, electrically conductive material in a fixed spatial relationship having a center-to-center spacing between two millimeters and six millimeters at tips of the electrodes configured for application to a periodontal complex, or to tissue surrounding the periodontal complex, of a single tooth;
    an electrical circuit configured for electrical connection to the at least two electrodes, the electrical circuit having an output providing an electrical stimulus comprising a waveform in accordance with stimulation parameters.

2. The device of claim 1, wherein the electrical stimulus is a therapeutically effective electrical stimulus for a periodontal complex of a tooth.

3. The device of claim 2, wherein the electrical stimulus is a therapeutically effective electrical stimulus for relieving periodontal pain.

4. The device of claim 2, wherein the electrical stimulus is a therapeutically effective electrical stimulus for affecting tooth movement.

5. The device of claim 1, further comprising a housing configured to be handheld and wherein the at least two electrodes are mounted in a first end of the housing.

6. The device of claim 5, wherein the at least two electrodes comprises:
   a base having a first mechanical connector and a first electrical connection, wherein the at least two electrodes are mounted in the base; and
   wherein the housing has a second mechanical connector having a mating configuration with the first mechanical connector of the base and a second electrical connection having a mating configuration with the first electrical connection of the base;
   whereby the base is removably connectable to the housing.

7. The device of claim 6, wherein the electrical circuit is mounted in the housing and the output of the electrical circuit is connected to the second electrical connection of the housing.

8. The device of claim 5, wherein the electrical circuit is mounted in the housing.

9. The device of claim 1, wherein the switch is a mechanical switch.

10. The device of claim 1, wherein the switch is an electromechanical switch.

11. The device of claim 1, wherein the waveform comprises a plurality of pulses having a pulse frequency.

12. The device of claim 11, wherein the waveform comprises a first plurality of pulses of a positive polarity at the pulse frequency in a first envelope, and a second plurality of pulses of a negative polarity at the pulse frequency in a second envelope, and a transition between the first and second plurality of envelopes occurring at a transition frequency.

13. The device of claim 11, wherein the pulse frequency is in a range of 1 kHz to 12 kHz.

14. The device of claim 1, wherein the predetermined stimulation parameters comprises a current of the electrical stimulus, and wherein the current is less than ten milliamperes.

15. The device of claim 1, wherein the predetermined stimulation parameters comprises a duration of the electrical stimulus, and wherein the duration is an amount of time greater than ten seconds and less than twenty minutes.

16. A process for electrical stimulation of one or more components of a periodontal complex, or of tissue surrounding the periodontal complex, of a single tooth, comprising:
   placing electrodes of a device on a periodontal complex, or to tissue surrounding the periodontal complex, of a single tooth, the electrodes comprising at least two electrodes of a rigid, electrically conductive material in a fixed spatial relationship having a center-to-center spacing between two millimeters and six millimeters at tips of the electrodes; and
   activating the device to generate an electrical stimulus while the electrodes of the device are placed.

17. The process of claim 16, further comprising moving the electrodes on the gingiva and along a periodontal ligament of a root structure of the single tooth.

18. The process of claim 16 further comprising maintaining the electrodes substantially stationary.

19. The process of claim 16, wherein placing the electrodes comprises placing the electrodes on enamel or dentin of the single tooth.

* * * * *

UNITED STATES PATENT AND TRADEMARK OFFICE
CERTIFICATE OF CORRECTION

| | |
|---|---|
| PATENT NO. | : 11,969,590 B2 |
| APPLICATION NO. | : 17/353887 |
| DATED | : April 30, 2024 |
| INVENTOR(S) | : Cosmo Haralambidis |

It is certified that error appears in the above-identified patent and that said Letters Patent is hereby corrected as shown below:

In the Claims

In Column 16, Line 24, in Claim 17, after "on" delete "the".

Signed and Sealed this
Twenty-fifth Day of June, 2024

Katherine Kelly Vidal
*Director of the United States Patent and Trademark Office*